US008785465B2

(12) United States Patent
Trullinger et al.

(10) Patent No.: US 8,785,465 B2
(45) Date of Patent: Jul. 22, 2014

(54) PESTICIDAL PYRIMIDINE COMPOUNDS

(71) Applicant: Dow AgroSciences LLC, Indianapolis, IN (US)

(72) Inventors: Tony K. Trullinger, Westfield, IN (US); Timothy C. Johnson, Indianapolis, IN (US); Ricky Hunter, Westfield, IN (US)

(73) Assignee: Dow AgroSciences, L.L.C., Indianapolis, IN (US)

( * ) Notice: Subject to any disclaimer, the term of this patent is extended or adjusted under 35 U.S.C. 154(b) by 0 days.

(21) Appl. No.: 14/063,898

(22) Filed: Oct. 25, 2013

(65) Prior Publication Data

US 2014/0134271 A1     May 15, 2014

Related U.S. Application Data

(60) Provisional application No. 61/725,056, filed on Nov. 12, 2012.

(51) Int. Cl.
 *A01N 43/54* (2006.01)
 *A61K 31/505* (2006.01)

(52) U.S. Cl.
 CPC ...................................... *A01N 43/54* (2013.01)
 USPC .......................................... 514/272; 544/320

(58) Field of Classification Search
 CPC ............................. A61K 31/506; C07D 239/52
 USPC .......................................... 544/320; 514/272
 See application file for complete search history.

(56) References Cited

U.S. PATENT DOCUMENTS

| | | | |
|---|---|---|---|
| 3,755,347 A | | 8/1973 | Guillot et al. |
| 4,684,395 A | * | 8/1987 | Levitt ............................ 504/214 |
| 4,859,699 A | | 8/1989 | Carney |
| 5,847,126 A | * | 12/1998 | Philipp et al. .................. 544/65 |
| 6,645,990 B2 | | 11/2003 | Askew et al. |
| 8,013,154 B2 | | 9/2011 | Niyaz et al. |
| 8,455,649 B2 | | 6/2013 | Niyaz et al. |
| 8,507,671 B2 | | 8/2013 | Niyaz et al. |
| 2009/0093486 A1 | | 4/2009 | Niyaz |

FOREIGN PATENT DOCUMENTS

| | | | |
|---|---|---|---|
| DE | 4304288 A1 | * | 8/1994 |
| WO | 2012/034961 A1 | | 3/2012 |
| WO | WO 2012034961 A1 | * | 3/2012 |

OTHER PUBLICATIONS

International Search Report dated Mar. 19, 2014 from application No. PCT/US2013/066952.

* cited by examiner

*Primary Examiner* — James O Wilson
*Assistant Examiner* — Alexander R Pagano
(74) *Attorney, Agent, or Firm* — Carl D. Corvin; Maschoff Brennan

(57) ABSTRACT

Pyrimidine compounds and their use in controlling pests such as insects and other invertebrates are provided. Further embodiments, forms, objects, features, advantages, aspects and benefits shall become apparent from the description.

13 Claims, No Drawings

PESTICIDAL PYRIMIDINE COMPOUNDS

CROSS-REFERENCE TO RELATED APPLICATIONS

The present application claims priority to U.S. Provisional Patent Application No. 61/725,056 filed on Nov. 12, 2012, the content of which is incorporated herein by references in its entirety.

FIELD OF THE INVENTION

The present application concerns novel pyrimidine compounds and their use in controlling pests such as insects and other invertebrates. The present application also concerns novels procedures for preparing these compounds, pesticide compositions including these compounds, and methods of controlling pests including insects using these compounds.

BACKGROUND OF THE INVENTION

Pests cause millions of human deaths around the world each year. Furthermore, there are more than ten thousand species of pests that cause losses in agriculture. The worldwide agricultural losses amount to billions of U.S. dollars each year. Pests, such as termites, are also known to cause damage to all kinds of private and public structures resulting in billions of U.S. dollars in losses each year. Pests also eat and adulterate stored food. The world-wide stored food losses amount to billions of U.S. dollars each year, but more importantly, deprive people of needed food.

Certain pests have or are developing resistance to one or more pesticides in current use. Hundreds of pest species are resistant to one or more pesticides. Accordingly, there exists a continuous need for new pesticides and for processes for forming such pesticides.

SUMMARY OF THE INVENTION

One embodiment disclosed herein concerns compounds useful for the control of pests such as insects. Another embodiment concerns compounds according to formula (I)

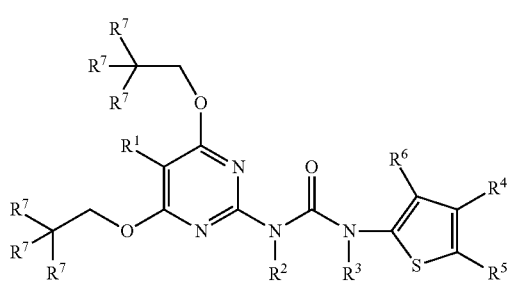

(I)

wherein:

$R^1$ is selected from the group consisting of hydrogen and halogen;

$R^2$ is selected from the group consisting of hydrogen, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_1$-$C_6$ acyl, substituted or unsubstituted $C_1$-$C_6$ carboalkoxy, carboxylic acid, substituted or unsubstituted $C_2$-$C_6$ alkenyloxy, substituted or unsubstituted $C_1$-$C_6$ alkoxy, substituted or unsubstituted $C_3$-$C_6$ alkynyl, substituted or unsubstituted $C_3$-$C_6$ alkynyloxy, substituted or unsubstituted $C_3$-$C_{10}$ aryl, substituted or unsubstituted $C_1$-$C_{10}$ aryloxy, substituted or unsubstituted $C_3$-$C_{10}$ cycloalkenyl, substituted or unsubstituted $C_3$-$C_{10}$ cycloalkenyloxy, substituted or unsubstituted $C_3$-$C_{10}$ cycloalkyl, substituted or unsubstituted $C_3$-$C_{10}$ cycloalkoxy, halo, and substituted or unsubstituted $C_1$-$C_{10}$ heterocyclyl;

$R^3$ is selected from the group consisting of hydrogen, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_3$-$C_6$ acyl, substituted or unsubstituted $C_1$-$C_6$ carboalkoxy, carboxylic acid, substituted or unsubstituted $C_2$-$C_6$ alkenyloxy, substituted or unsubstituted $C_1$-$C_6$ alkoxy, substituted or unsubstituted $C_3$-$C_6$ alkynyl, substituted or unsubstituted $C_3$-$C_6$ alkynyloxy, substituted or unsubstituted $C_3$-$C_1$ aryl, substituted or unsubstituted $C_3$-$C_1$ aryloxy, substituted or unsubstituted $C_3$-$C_{10}$ cycloalkenyl, substituted or unsubstituted $C_3$-$C_1$ cycloalkenyloxy, substituted or unsubstituted $C_3$-$C_{10}$ cycloalkyl, substituted or unsubstituted $C_3$-$C_1$ cycloalkoxy, halo, and substituted or unsubstituted $C_1$-$C_{10}$ heterocyclyl;

each of $R^4$, $R^5$, and $R^6$ is independently selected from the group consisting of hydrogen, halogen, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_1$-$C_6$ acyl, substituted or unsubstituted $C_1$-$C_6$ carboalkoxy, carboxylic acid, substituted or unsubstituted $C_2$-$C_6$ alkenyloxy, substituted or unsubstituted $C_1$-$C_6$ alkoxy, substituted or unsubstituted $C_3$-$C_6$ alkynyl, substituted or unsubstituted $C_3$-$C_6$ alkynyloxy, substituted or unsubstituted $C_3$-$C_{10}$ aryl, substituted or unsubstituted $C_1$-$C_{10}$ aryloxy, substituted or unsubstituted $C_3$-$C_{10}$ cycloalkenyl, substituted or unsubstituted $C_3$-$C_{10}$ cycloalkenyloxy, substituted or unsubstituted $C_3$-$C_{10}$ cycloalkyl, substituted or unsubstituted $C_3$-$C_{10}$ cycloalkoxy, substituted or unsubstituted $C_1$-$C_6$ nitriles, substituted or unsubstituted $C_1$-$C_6$ amides, substituted or unsubstituted $C_1$-$C_6$ amines, S (substituted or unsubstituted $C_1$-$C_6$ alkyl), $S(O)_n$ (substituted or unsubstituted $C_1$-$C_6$ alkyl) wherein n=0, 1 or 2, and substituted or unsubstituted $C_1$-$C_{10}$ heterocyclyl; and each $R^7$ is independently selected from the group consisting of halogen, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_1$-$C_6$ acyl, substituted or unsubstituted $C_1$-$C_6$ carboalkoxy, carboxylic acid, substituted or unsubstituted substituted or unsubstituted $C_2$-$C_6$ alkenyloxy, substituted or unsubstituted $C_1$-$C_6$ alkoxy, substituted or unsubstituted $C_3$-$C_6$ alkynyl, substituted or unsubstituted $C_3$-$C_6$ alkynyloxy, substituted or unsubstituted $C_3$-$C_{10}$ aryl, substituted or unsubstituted $C_1$-$C_{10}$ aryloxy, substituted or unsubstituted $C_3$-$C_{10}$ cycloalkenyl, substituted or unsubstituted $C_3$-$C_{10}$ cycloalkenyloxy, substituted or unsubstituted $C_3$-$C_{10}$ cycloalkyl, substituted or unsubstituted $C_3$-$C_{10}$ cycloalkoxy, and substituted or unsubstituted $C_1$-$C_{10}$ heterocyclyl, wherein each substituted or unsubstituted substituent may be independently substituted with one or more of the following substituents F, Cl, Br, I, CN, NO$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, C$_1$-C$_6$ haloalkylthio, S(=O)$_{n1}$C$_1$-C$_6$ alkyl (where n1=0-2), S(=O)$_{n1}$C$_1$-C$_6$ haloalkyl (where n1=0-2), OSO$_2$C$_1$-C$_6$ haloalkyl, C(=O)OC$_1$-C$_6$ alkyl, C(=O)C$_1$-C$_6$ alkyl, C(=O)C$_1$-C$_6$ haloalkyl, aryl, C$_1$-C$_6$ hydroxyalkyl, CO$_2$R$^8$, wherein R$^8$ is a C$_1$-C$_6$ alkyl, and heterocyclyl.

More particular but non-limiting forms of compounds according to formula (I) include the following classes:

(1) Compounds of formula (I) wherein R$^1$ represents H or halogen.

(2) Compounds of formula (I) wherein R$^2$ represents H or a substituted or unsubstituted C$_1$-C$_6$ alkoxy.

(3) Compounds of formula (I) wherein R$^3$ represents H, a substituted or unsubstituted C$_1$-C$_6$ alkyl, or a substituted or unsubstituted C$_1$-C$_6$ alkoxy.

(4) Compounds of formula (I) wherein R$^4$ represents H, halogen, a substituted or unsubstituted C$_1$-C$_6$ alkyl, a substituted or unsubstituted C$_1$-C$_6$ nitrile, or a substituted or unsubstituted C$_3$-C$_{10}$ cycloalkenyl, or wherein R$^4$ represents H, halogen, a substituted or unsubstituted C$_1$-C$_6$ alkyl, or a substituted or unsubstituted C$_3$-C$_{10}$ cycloalkenyl.

(5) Compounds of formula (I) wherein R$^5$ represents H, halogen, a substituted or unsubstituted C$_1$-C$_6$ haloalkyl, a substituted or unsubstituted C$_1$-C$_6$ alkyl, or a substituted or unsubstituted C$_1$-C$_6$ nitrile.

(6) Compounds of formula (I) wherein R$^6$ represents H, halogen, a substituted or unsubstituted C$_1$-C$_6$ alkyl, or a substituted or unsubstituted C$_1$-C$_6$ alkoxy.

(7) Compounds of formula (I) wherein R$^7$ represents halogen.

It should be understood by those skilled in the art that one or more combinations of the above described classes 1-7 of the compound according to formula (I) are possible. Stated alternatively, in some more particular but non-limiting forms of compounds according to formula (I), one or more or all of R$^1$-R$^7$ may represent a substituent listed in a respective one of classes 1-7.

Additional, more particular but non-limiting forms of compounds according to formula (I) include the following classes:

(8) Compounds of formula (I) wherein R$^1$ represents H or halogen.

(9) Compounds of formula (I) wherein R$^2$ represents H or a substituted or unsubstituted C$_1$-C$_6$ alkoxy.

(10) Compounds of formula (I) wherein R$^3$ represents H, a substituted or unsubstituted C$_1$-C$_6$ alkyl, or a substituted or unsubstituted C$_1$-C$_6$ alkoxy.

(11) Compounds of formula (I) wherein R$^4$ represents H.

(12) Compounds of formula (I) wherein R$^5$ represents a substituted or unsubstituted C$_1$-C$_6$ haloalkyl such as CF$^3$.

(13) Compounds of formula (I) wherein R$^6$ represents H.

(14) Compounds of formula (I) wherein R$^7$ represents halogen.

It should be understood by those skilled in the art that one or more combinations of the above described classes 9-14 of the compound according to formula (I) are possible. Stated alternatively, in some more particular but non-limiting forms of compounds according to formula (I), one or more or all of R$^1$-R$^7$ may represent a substituent listed in a respective one of classes 9-14.

Another embodiment concerns compounds according to formula (I) having the following structure:

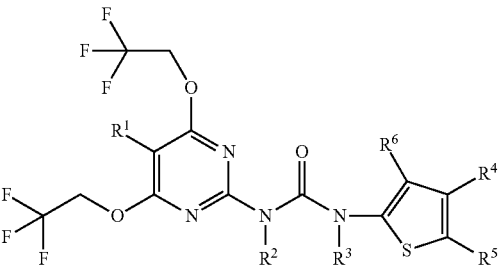

wherein:

R$^1$ represents H or halogen;

R$^2$ represents H, CH$_2$OCH$_3$, CH$_2$OC(=O)CH$_3$ or CH$_2$OCH$_2$R$^9$, wherein R$^9$ represents

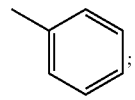;

R$^3$ represents H, methyl, CH$_2$OCH$_3$, or CH$_2$OCH$_2$R$^9$, wherein R$^9$ represents

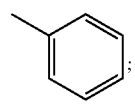;

R$^4$ represents H, halogen, methyl, CN, or

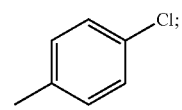;

R$^5$ represents H, halogen, CN, methyl, ethyl or C(R$^{10}$)$_3$, wherein R$^{10}$ represents halogen; and R$^6$ represents H, halogen, methyl or OCH$_3$.

More particular but non-limiting forms of this embodiment include the following classes:

(15) Compounds where R$^5$ represents CF$_3$.

(16) Compounds where R$^1$ represents H or F.

(17) Compounds where R$^4$ and R$^6$ represent H.

(18) Compounds where R$^2$ and R$^3$ represent H.

It should be understood by those skilled in the art that one or more combinations of the above described classes 15-18 are possible.

In further, more particular but non-limiting forms of this embodiment, R$^1$-R$^6$ represent the following:

R$^1$ represents H or F;

R$^2$ represents H, CH$_2$OCH$_3$, CH$_2$C(=O)CH$_3$ or CH$_2$OCH$_2$R$^9$, wherein R$^9$ represents

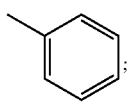

$R^3$ represents H, methyl or $CH_2OCH_3$;
$R^4$ represents H, methyl, Cl or

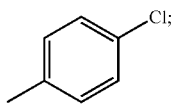

$R^5$ represents H, Cl, CN, methyl or $CF_3$; and
$R^6$ represents H, methyl, Cl or $OCH_3$.

In even further, more particular but non-limiting forms of this embodiment, $R^1$-$R^6$ represent the following:
$R^1$ represents H or F;
$R^2$ represents H, $CH_2OCH_3$, $CH_2C(=O)CH_3$ or $CH_2OCH_2R^9$, wherein $R^9$ represents

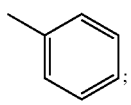

$R^3$ represents H, methyl or $CH_2OCH_3$;
$R^4$ represents H;
$R^5$ represents $CF_3$; and
$R^6$ represents H.

Further aspects, embodiments, forms, features, benefits, objects and advantages shall become apparent from the detailed description provided herewith.

DETAILED DESCRIPTION OF THE INVENTION

For purposes of promoting an understanding of the invention, reference will now be made to the following embodiments and specific language will be used to describe the same. It will nevertheless be understood that no limitation of the scope of the invention is thereby intended, such alterations and further modifications in the described subject matter, and such further applications of the principles of the invention as described herein being contemplated as would normally occur to one skilled in the art to which the invention relates.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, propyl, isopropyl, butyl, and tert-butyl.

"Alkynyl" means an acyclic, unsaturated (at least one carbon-carbon triple bond), branched or unbranched, substituent consisting of carbon and hydrogen, for example, ethynyl, propargyl, butyryl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" or "Halogen" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. Examples of aromatic heterocyclyls include, but are not limited to, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, tetrahydrofuranyl, and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

One embodiment disclosed herein is related to novel pyrimidine compounds and their use in controlling pests such as insects and other invertebrates. Another more particular but non-exclusive embodiment is related to compounds according to formula (I):

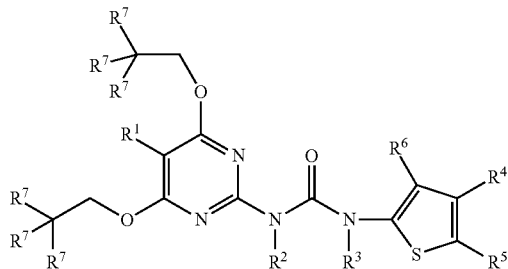

wherein $R^1$ is selected from the group consisting of hydrogen and halogen;

$R^2$ is selected from the group consisting of hydrogen, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_1$-$C_6$ acyl, substituted or unsubstituted $C_1$-$C_6$ carboalkoxy, carboxylic acid, substituted or unsubstituted $C_2$-$C_6$ alkenyloxy, substituted or unsubstituted $C_1$-$C_6$ alkoxy, substituted or unsubstituted $C_3$-$C_6$ alkynyl, substituted or unsubstituted $C_3$-$C_6$ alkynyloxy, substituted or unsubstituted $C_3$-$C_{10}$ aryl, substituted or unsubstituted $C_1$-$C_{10}$ aryloxy, substituted or unsubstituted $C_3$-$C_{10}$ cycloalkenyl, substituted or unsubstituted $C_3$-$C_{10}$ cycloalkenyloxy, substituted or unsubstituted $C_3$-$C_{10}$ cycloalkyl, substituted or unsubstituted $C_3$-$C_{10}$ cycloalkoxy, halo, and substituted or unsubstituted $C_1$-$C_{10}$ heterocyclyl;

$R^3$ is selected from the group consisting of hydrogen, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_3$-$C_6$ acyl, substituted or unsubstituted $C_1$-$C_6$ carboalkoxy, carboxylic acid, substituted or unsubstituted $C_2$-$C_6$ alkenyloxy, substituted or unsubstituted $C_1$-$C_6$ alkoxy, substituted or unsubstituted $C_3$-$C_6$ alkynyl, substituted or unsubstituted $C_3$-$C_6$ alkynyloxy, substituted or unsubstituted $C_3$-$C_{10}$ aryl, substituted or unsubstituted $C_3$-$C_{10}$ aryloxy, substituted or unsubstituted $C_3$-$C_{10}$ cycloalkenyl, substituted or unsubstituted $C_3$-$C_{10}$ cycloalkenyloxy, substituted or unsubstituted $C_3$-$C_{10}$ cycloalkyl, substituted or unsubstituted $C_3$-$C_{10}$ cycloalkoxy, halo, and substituted or unsubstituted $C_1$-$C_{10}$ heterocyclyl;

each of $R^4$, $R^5$, and $R^6$ is independently selected from the group consisting of hydrogen, halogen, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_1$-$C_6$ acyl, substituted or unsubstituted $C_1$-$C_6$ carboalkoxy, carboxylic acid, substituted or unsubstituted $C_2$-$C_6$ alkenyloxy, substituted or unsubstituted $C_1$-$C_6$ alkoxy, substituted or unsubstituted $C_3$-$C_6$ alkynyl, substituted or unsubstituted $C_3$-$C_6$ alkynyloxy, substituted or unsubstituted $C_3$-$C_{10}$ aryl, substituted or unsubstituted $C_1$-$C_{10}$ aryloxy, substituted or unsubstituted $C_3$-$C_{10}$ cycloalkenyl, substituted or unsubstituted $C_3$-$C_{10}$ cycloalkenyloxy, substituted or unsubstituted $C_3$-$C_{10}$ cycloalkyl, substituted or unsubstituted $C_3$-$C_{10}$ cycloalkoxy, substituted or unsubstituted $C_1$-$C_6$ nitriles, substituted or unsubstituted $C_1$-$C_6$ amides, substituted or unsubstituted $C_1$-$C_6$ amines, S (substituted or unsubstituted $C_1$-$C_6$ alkyl), $S(O)_n$ (substituted or unsubstituted $C_1$-$C_6$ alkyl) wherein n=0, 1 or 2, and substituted or unsubstituted $C_1$-$C_{10}$ heterocyclyl; and each $R^7$ is independently selected from the group consisting of halogen, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_1$-$C_6$ acyl, substituted or unsubstituted $C_1$-$C_6$ carboalkoxy, carboxylic acid, substituted or unsubstituted substituted or unsubstituted $C_2$-$C_6$ alkenyloxy, substituted or unsubstituted $C_1$-$C_6$ alkoxy, substituted or unsubstituted $C_3$-$C_6$ alkynyl, substituted or unsubstituted $C_3$-$C_6$ alkynyloxy, substituted or unsubstituted $C_3$-$C_{10}$ aryl, substituted or unsubstituted $C_1$-$C_{10}$ aryloxy, substituted or unsubstituted $C_3$-$C_{10}$ cycloalkenyl, substituted or unsubstituted $C_3$-$C_{10}$ cycloalkenyloxy, substituted or unsubstituted $C_3$-$C_{10}$ cycloalkyl, substituted or unsubstituted $C_3$-$C_{10}$ cycloalkoxy, and substituted or unsubstituted $C_1$-$C_{10}$ heterocyclyl, wherein each substituted or unsubstituted substituent may be independently substituted with one or more of the following substituents F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, $C(=O)OC_1$-$C_6$ alkyl, $C(=O)C_1$-$C_6$ alkyl, $C(=O)C_1$-$C_6$ haloalkyl, aryl, $C_1$-$C_6$ hydroxyalkyl, $CO_2R^8$, wherein $R^8$ is $C_1$-$C_6$ alkyl, and heterocyclyl. More particular but non-limiting forms of compounds according to formula (I) include the following classes:

(1) Compounds of formula (I) wherein $R^1$ represents H or halogen.

(2) Compounds of formula (I) wherein $R^2$ represents H or a substituted or unsubstituted $C_1$-$C_6$ alkoxy.

(3) Compounds of formula (I) wherein $R^3$ represents H, a substituted or unsubstituted $C_1$-$C_6$ alkyl, or a substituted or unsubstituted $C_1$-$C_6$ alkoxy.

(4) Compounds of formula (I) wherein $R^4$ represents H, halogen, a substituted or unsubstituted $C_1$-$C_6$ alkyl, a substituted or unsubstituted $C_1$-$C_6$ nitrile, or a substituted or unsubstituted $C_3$-$C_{10}$ cycloalkenyl, or wherein $R^4$ represents H, halogen, a substituted or unsubstituted $C_1$-$C_6$ alkyl, or a substituted or unsubstituted $C_3$-$C_{10}$ cycloalkenyl.

(5) Compounds of formula (I) wherein $R^5$ represents H, halogen, a substituted or unsubstituted $C_1$-$C_6$ haloalkyl, a substituted or unsubstituted $C_1$-$C_6$ alkyl, or a substituted or unsubstituted $C_1$-$C_6$ nitrile.

(6) Compounds of formula (I) wherein $R^6$ represents H, halogen, a substituted or unsubstituted $C_1$-$C_6$ alkyl, or a substituted or unsubstituted $C_1$-$C_6$ alkoxy.

(7) Compounds of formula (I) wherein $R^7$ represents halogen.

It should be understood by those skilled in the art that one or more combinations of the above described classes 1-7 of the compound according to formula (I) are possible. Stated alternatively, in some more particular but non-limiting forms of compounds according to formula (I), one or more or all of $R^1$-$R^7$ may represent a substituent listed in a respective one of classes 1-7.

Additional, more particular but non-limiting forms of compounds according to formula (I) include the following classes:

(8) Compounds of formula (I) wherein $R^1$ represents H or halogen.

(9) Compounds of formula (I) wherein $R^2$ represents H or a substituted or unsubstituted $C_1$-$C_6$ alkoxy.

(10) Compounds of formula (I) wherein $R^3$ represents H, a substituted or unsubstituted $C_1$-$C_6$ alkyl, or a substituted or unsubstituted $C_1$-$C_6$ alkoxy.

(11) Compounds of formula (I) wherein $R^4$ represents H.

(12) Compounds of formula (I) wherein $R^5$ represents a substituted or unsubstituted $C_1$-$C_6$ haloalkyl such as $CF^3$.

(13) Compounds of formula (I) wherein $R^6$ represents H.

(14) Compounds of formula (I) wherein $R^7$ represents halogen.

It should be understood by those skilled in the art that one or more combinations of the above described classes 9-14 of the compound according to formula (I) are possible. Stated alternatively, in some more particular but non-limiting forms of compounds according to formula (I), one or more or all of $R^1$-$R^7$ may represent a substituent listed in a respective one of classes 9-14.

Another embodiment concerns compounds according to formula (I) having the following structure:

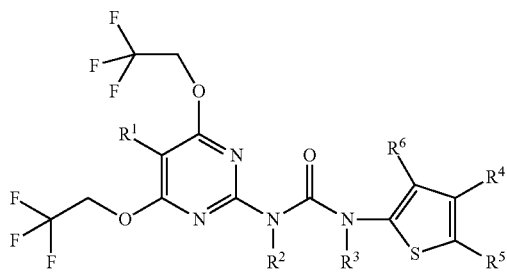

wherein:

$R^1$ represents H or halogen;

$R^2$ represents H, $CH_2OCH_3$, $CH_2C(=O)CH_3$ or $CH_2OCH_2R^9$, wherein $R^9$ represents

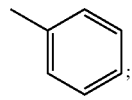;

$R^3$ represents H, methyl, $CH_2OCH_3$, or $CH_2OCH_2R^9$, wherein $R^9$ represents

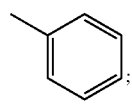;

$R^4$ represents H, halogen, methyl, CN, or

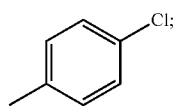;

$R^5$ represents H, halogen, CN, methyl, ethyl or $C(R^{10})_3$, wherein $R^{10}$ represents halogen; and $R^6$ represents H, halogen, methyl or $OCH_3$.

More particular but non-limiting forms of this embodiment include the following classes:

(15) Compounds where $R^5$ represents $CF_3$.

(16) Compounds where $R^1$ represents H or F.

(17) Compounds where $R^4$ and $R^6$ represent H.

(18) Compounds where $R^2$ and $R^3$ represent H.

It should be understood by those skilled in the art that one or more combinations of the above described classes 15-18 are possible.

In further, more particular but non-limiting forms of this embodiment, $R^1$-$R^6$ represent the following:

$R^1$ represents H or F;

$R^2$ represents H, $CH_2OCH_3$, $CH_2C(=O)CH_3$ or $CH_2OCH_2R^9$, wherein $R^9$ represents

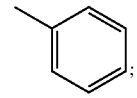;

$R^3$ represents H, methyl or $CH_2OCH_3$;

$R^4$ represents H, methyl, Cl or

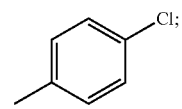;

$R^5$ represents H, Cl, CN, methyl or $CF_3$; and $R^6$ represents H, methyl, Cl or $OCH_3$.

In even further, more particular but non-limiting forms of this embodiment, $R^1$-$R^6$ represent the following:

$R^1$ represents H or F;

$R^2$ represents H, $CH_2OCH_3$, $CH_2C(=O)CH_3$ or $CH_2OCH_2R^9$, wherein $R^9$ represents

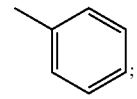;

$R^3$ represents H, methyl or $CH_2OCH_3$;

$R^4$ represents H;

$R^5$ represents $CF_3$; and $R^6$ represents H.

Pesticidally Acceptable Acid Addition Salts, Salt Derivatives, Solvates, Ester Derivatives, Polymorphs, Isotopes and Radionuclides Compounds according to formula (I) may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Exemplary cations include sodium, potassium, and magnesium.

Compounds according to formula (I) may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Compounds according to formula (I) may be formulated into stable complexes with a solvent, such that the complex remains intact after the non-complexed solvent is removed. These complexes are often referred to as "solvates." However, in one particular form, stable hydrates are formed with water as the solvent.

Compounds according to formula (I) may be made into ester derivatives. These ester derivatives can then be applied in the same manner as the molecules disclosed in this document is applied.

Compounds according to formula (I) may be made as various crystal polymorphs. Polymorphism is important in the development of agrochemicals since different crystal polymorphs or structures of the same molecule can have vastly different physical properties and biological performances.

Compounds according to formula (I) may be made with different isotopes. Particular but non-limiting examples of such are molecules having $^2H$ (also known as deuterium) in place of $^1H$.

Compounds according to formula (I) may be made with different radionuclides. Particular but non-limiting examples of such are molecules having $^{14}C$.

Combinations

Compounds according to formula (I) may also be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, or virucidal properties. Additionally, compounds according to formula (I) may also be used in combination (such as, in a compositional mixture, or a simultaneous or sequential application) with compounds that are antifeedants, bird repellents, chemosterilants, herbicide safeners, insect attractants, insect repellents, mammal repellents, mating disrupters, plant activators, plant growth regulators, or synergists. Examples of such compounds in the above groups that may be used with compounds according to formula (I) are—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butomethyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, amino cyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluoron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfuram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butomethyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyrsulfuron, flupyrsulfuron-methyl, flupyrsulfuron-methyl-sodium, fluquinconazole, flurazole, flurenol, flurenol-butyl, flurenol-methyl, fluridone, fluorochloridone, fluoroxypyr, fluoroxypyr-butomethyl, fluoroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexylure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluoron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfuram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluoron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluoron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council, or its prior or more recent editions.

Biopesticides

Compounds according to formula (I) may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinernema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, compounds according to formula (I) may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

Compounds according to formula (I) may also be used in combination (such as in a compositional mixture, or a simultaneous or sequential application) with one or more of the following:
1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl) ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl)hydrazone;
15. N-ethyl-2,2-dichloro-1-methylcyclopropane-carboxamide-2-(2,6-dichloro-α,α,α-trifluoro-p-tolyl)hydrazone nicotine;
16. O-{(E-)[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)] phenyl mesylate; and
20. N-Ethyl-2,2-dichloro-1-methylcyclopropanecarboxamide-2-(2,6-dichloro-alpha,alpha,alpha-trifluoro-p-tolyl) hydrazone.

Synergistic Mixtures

Compounds according to formula (I) may be used with certain active compounds to form synergistic mixtures where the mode of action of such compounds compared to the mode of action of compounds according to formula (I) are the same, similar, or different. Examples of modes of action include, but are not limited to: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs). Generally, weight ratios of compounds according to formula (I) in a synergistic mixture with another compound are from about 10:1 to about 1:10, in another embodiment from about 5:1 to about 1:5, and in another embodiment from about 3:1, and in another embodiment about 1:1.

Formulations

A pesticide may not suitable for application in its pure form. It may be necessary to add other substances so that the pesticide can be used at the required concentration and in an appropriate form, permitting ease of application, handling, transportation, storage, and maximum pesticide activity. Thus, pesticides can be formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph no 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication No. 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the compounds disclosed herein are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspo-emulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of $C_9$ and $C_{10}$ aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, compounds according to formula (I) may be used to control pests e.g. ants, aphids, beetles, bristletails, cockroaches, crickets, earwigs, fleas, flies, grasshoppers, leafhoppers, lice, locusts, mites, moths, nematodes, scales, symphylans, termites, thrips, ticks, wasps, and whiteflies.

In another embodiment, the compounds according to formula (I) may be used to control pests in the Phyla Nematoda and/or Arthropoda.

In another embodiment, the compounds according to formula (I) may be used to control pests in the Subphyla Chelicerata, Myriapoda, and/or Hexapoda.

In another embodiment, the compounds according to formula (I) may be used to control pests in the Classes of Arachnida, Symphyla, and/or Insecta.

In another embodiment, the compounds according to formula (I) may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In another embodiment, the compounds according to formula (I) may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In another embodiment, the compounds according to formula (I) may be used to control pests of the Order Dermaptera.

In another embodiment, the compounds according to formula (I) may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*.

In another embodiment, the compounds according to formula (I) may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza bras-*

*sicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

In another embodiment, the compounds according to formula (I) may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Phiiaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis*, and *Zulia entrerriana*.

In another embodiment, the compounds according to formula (I) may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni*, and *Tapinoma sessile*.

In another embodiment, the compounds according to formula (I) may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

In another embodiment, the compounds according to formula (I) may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricans, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabs, Plodia interpunctella, Plutella xylostella, Polychrosis viteana, Prays endocarps, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae*, and *Zeuzera pyrina*.

In another embodiment, the compounds according to formula (I) may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae*, and *Trichodectes canis*.

In another embodiment, the compounds according to formula (I) may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderia furcata*.

In another embodiment, the compounds according to formula (I) may be used to control pests of the Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans*.

In another embodiment, the compounds according to formula (I) may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis*, and *Taeniothrips rhopalantennalis, Thrips hawaiiensis, Thrips nigropilosus, Thrips orientalis, Thrips tabaci*.

In another embodiment, the compounds according to formula (I) may be used to control pests of the Order Thysanura. A non-exhaustive list of particular genera includes, but is not limited to, *Lepisma* spp. and *Thermobia* spp.

In another embodiment, the compounds according to formula (I) may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyp hagotarsonemus latus, Rhipicephalus sanguineus, Sarcoptes scabiei, Tegolophus perseaflorae, Tetranychus urticae*, and *Varroa destructor*.

In another embodiment, the compounds according to formula (I) may be used to control pest of the Order Symphyla. A non-exhaustive list of particular sp. includes, but is not limited to, *Scutigerella immaculata*.

In another embodiment, the compounds according to formula (I) may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Compounds according to formula (I) are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a compound according to formula (I) is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a compound according to formula (I) include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The compounds according to formula (I) may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such compounds may be used during times when pest activity is low, such as before the plants that are growing begin to produce valuable agricultural commodities. Such times include the early planting season when pest pressure is usually low.

The compounds according to formula (I) can be applied to the foliar and fruiting portions of plants to control pests. The compounds will either come in direct contact with the pest, or the pest will consume the pesticide when eating leaf, fruit mass, or extracting sap, that contains the pesticide. The compounds according to formula (I) can also be applied to the soil, and when applied in this manner, root and stem feeding pests can be controlled. The roots can absorb a compound taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a compound according to formula (I).

The compounds according to formula (I) can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the compounds according to formula (I) may be desirable to control newly emerged larvae.

Systemic movement of pesticides in plants may be utilized to control pests on one portion of the plant by applying (for example by spraying an area) the compounds according to formula (I) to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the compounds according to formula (I) may further enhance the ability of a plant to better withstand stressful growing conditions. This results in a healthier, more vigorous plant, which can lead to higher yields at harvest time. Generally, about 1 gram of the compounds according to formula (I) to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the compounds according to formula (I) may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The compounds according to formula (I) may be used for controlling endoparasites and ectoparasites in the veterinary medicine sector or in the field of non-human animal keeping. The compounds according to formula (I) are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The compounds according to formula (I) may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The compounds according to formula (I) may also be used for controlling parasitic worms, especially of the intestine, in the animals listed above.

The compounds according to formula (I) may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The compounds according to formula (I) may also be used on such new invasive species to control them in such new environment.

The compounds according to formula (I) may also be used in an area where plants, such as crops, are growing (e.g. pre-planting, planting, pre-harvesting) and where there are low levels (even no actual presence) of pests that can commercially damage such plants. The use of such compounds in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A compound according to formula (I) can be tested to determine its efficacy against pests. Furthermore, mode of action studies can be conducted to determine if said compound has a different mode of action than other pesticides. Thereafter, such acquired data can be disseminated, such as by the internet, to third parties.

The compounds according to formula (I) will generally have a molecular mass of about 100 Daltons to about 1200 Daltons. However, it is generally preferred if the molecular mass is from about 120 Daltons to about 900 Daltons, and it is even more generally preferred if the molecular mass is from about 140 Daltons to about 600 Daltons.

EXAMPLES

The examples are for illustration purposes and are not to be construed as limiting the invention disclosed in this document to only the embodiments disclosed in these examples.

Starting materials, reagents, and solvents that were obtained from commercial sources were used without further purification Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw or ACD Name Pro. If such programs are unable to name a molecule, the molecule is named using conventional naming rules. $^1$H NMR spectral data are in ppm ($\delta$) and were recorded at 300, 400 or 600 MHz, and $^{13}$C NMR spectral data are in ppm ($\delta$) and were recorded at 75, 100 or 150 MHz, unless otherwise stated.

Compounds according to formula (I) can be prepared by the methods illustrated in Schemes I-IV below.

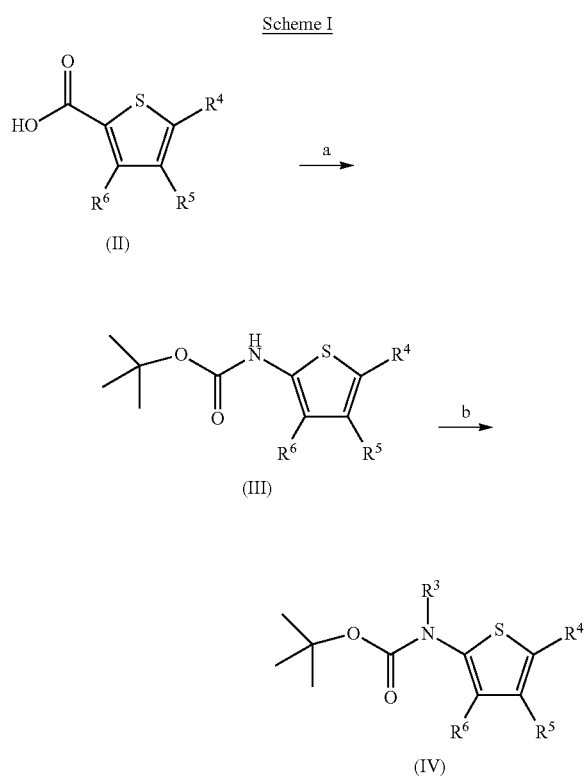

In Scheme I, compounds according to formula (III), where $R^4$, $R^5$ and $R^6$ are as previously defined, can be prepared as in step a, from compounds according to formula (II) through a Curtius rearrangement, using reagents such as diphenylphosphoryl azide in a solvent such as toluene and a base such as triethylamine in the presence of tert-butanol. Compounds according to formula (II) where $R^4$, $R^5$, and $R^6$ are as previously defined are available from a variety of different commercial sources. Compounds of formula (IV), where $R^3$ does not represent H but is otherwise as previously defined and each of $R^4$, $R^5$ and $R^6$ is as previously defined, can be prepared as in step b, from a compound according to formula (III) using a base such as sodium hydride in a solvent such as DMF and an alkylating reagent such as methyl iodide.

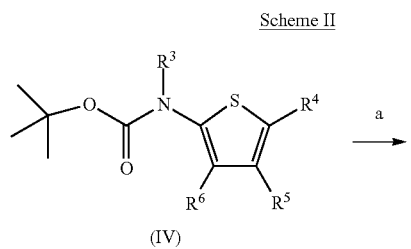

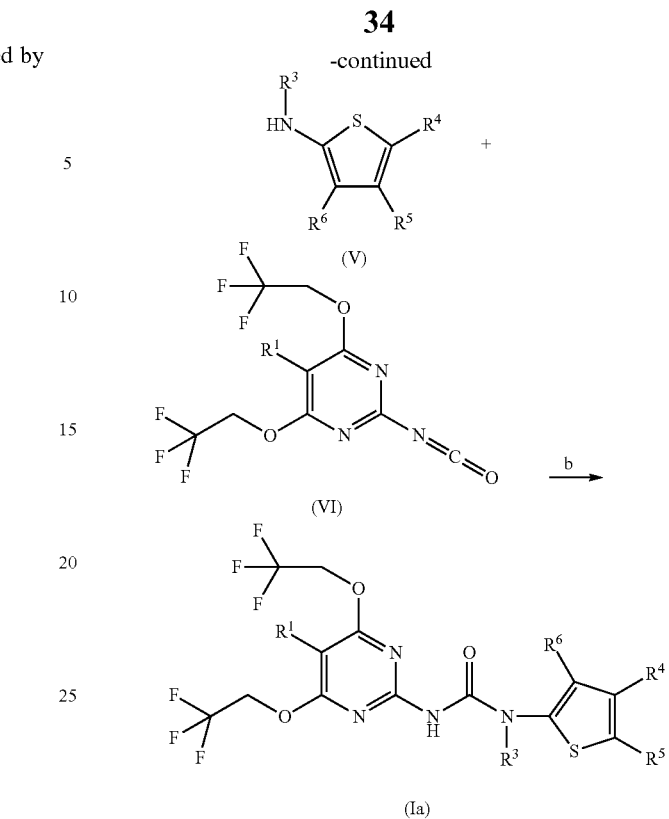

In Scheme II above, compounds according to formula (V) can be prepared from compounds according to formula (IV), where $R^3$ does not represent H but is otherwise as previously defined and each of $R^4$, $R^5$, and $R^6$ is as previously defined, as in step a using standard deprotecting conditions such as trifluoroacetic acid in methylene chloride. Compounds according to formula (Ia), where $R^2$ represents H, $R^3$ does not represent H but is otherwise as previously defined and each of $R^1$, $R^4$, $R^5$ and $R^6$ is as previously defined, can be prepared as in step b by combining compounds according to formula (V) with compounds according to formula (VI), where $R^1$ is as previously defined and $R^7$ represents F, in a solvent such as THF or methylene chloride. Compounds according to formula (VI), such as 2-isocyanato-4,6-bis(trifluoroethoxy)pyrimidine and 5-fluoro-2-isocyanato-4,6-bis(trifluoroethoxy)pyrimidine, can be prepared as disclosed in U.S. Pat. No. 8,013,154(B2), the contents of which are incorporated herein by reference in their entirety.

Scheme III

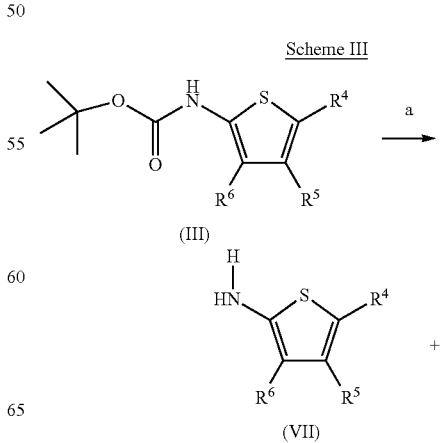

-continued

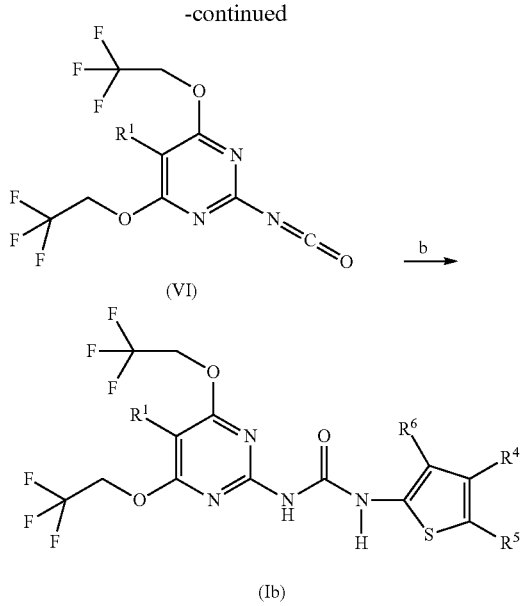

In Scheme III above, compounds according to formula (VII) can be prepared from compounds according to formula (III), where each of $R^4$, $R^5$, and $R^6$ is as previously defined, as in step a using standard deprotecting conditions such as trifluoroacetic acid in methylene chloride. Compounds according to formula (Ib), where each of $R^2$ and $R^3$ represents H and each of $R^1$, $R^4$, $R^5$ and $R^6$ is as previously defined, can be prepared as in step b by combining compounds according to formula (VII) with compounds according to formula (VI), where $R^1$ is as previously defined, in a solvent such as THF or methylene chloride.

Scheme IV

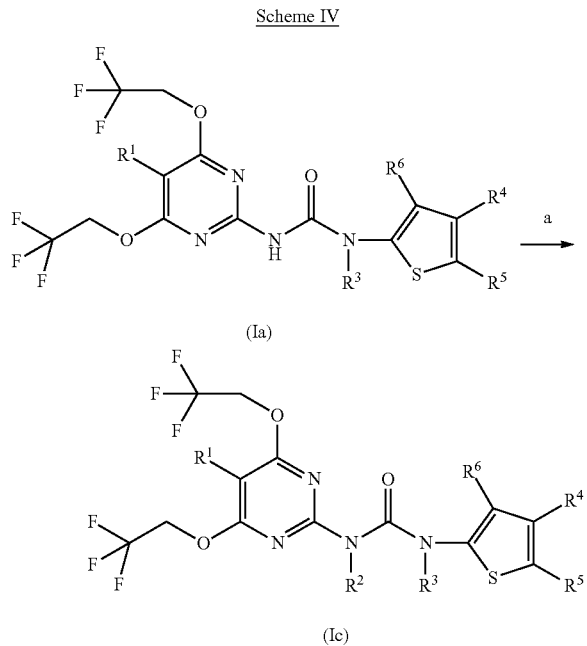

In Scheme IV above, compounds according to Formula (Ic), where $R^2$ and $R^3$ do not represent H but are as otherwise previously defined and each of $R^1$, $R^4$, $R^5$ and $R^6$ is as previously defined, can be prepared from compounds according to Formula (Ia), where $R^2$ represents H, $R^3$ does not represent H but is as otherwise previously defined and each of $R^1$, $R^4$, $R^5$ and $R^6$ is as previously defined, as in step a, using a base such as sodium hydride in a solvent such as THF, followed by reaction with an electrophilic reagent such as benzyloxymethyl chloride or other alkyl electrophile.

Scheme V

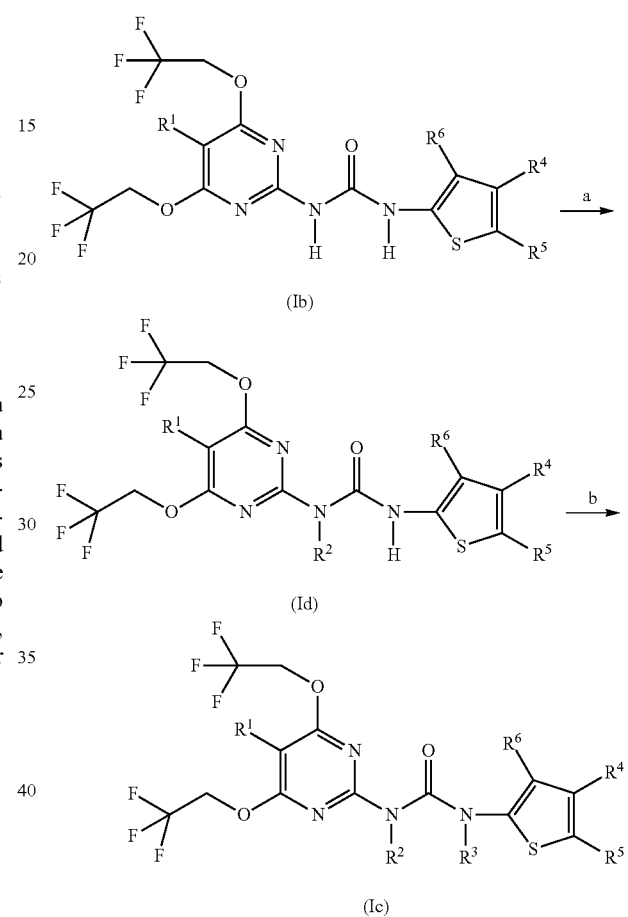

In Scheme V above, compounds according to formula (Id), where $R^2$ does not represent H but is otherwise as previously defined, $R^3$ represents H, and each of $R^1$, $R^4$, $R^5$ and $R^6$ is as previously defined, can be prepared from compounds according to formula (Ib), where $R^2$ and $R^3$ represent H and each of $R^1$, $R^4$, $R^5$ and $R^6$ is as previously defined, as in step a, using a base such as sodium hydride in a solvent such as THF, followed by reaction with an electrophilic reagent such as benzyloxymethyl chloride or other alkyl electrophile. Compounds according to formula (Ic), where $R^2$ and $R^3$ do not represent H but are otherwise as previously defined and each of $R^1$, $R^4$, $R^5$ and $R^6$ is as previously defined, can be prepared from compounds according to formula (Id) as in step b, using a base such as sodium hydride and a solvent such as THF, followed by reaction with an electrophilic reagent such as methyl iodide or other alkyl electrophile. Steps a and b can also be performed in one process whereby a compound according to formula (Ib) is treated with two or more equivalents of a base, such as sodium hydride, and then is treated with two or more equivalents of an electrophile, such as methyl iodide.

Scheme VI

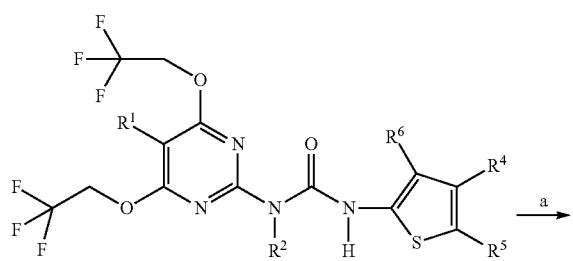

(Id)

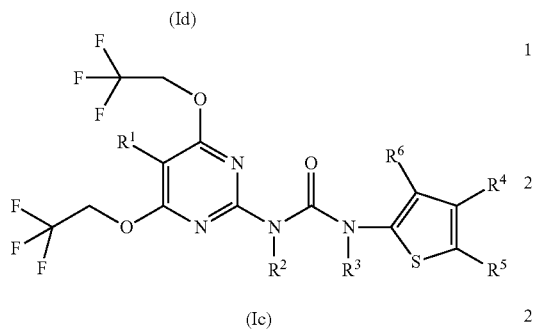

(Ic)

In Scheme VI above, compounds according to formula (Ic) where $R^2$ and $R^3$ do not represent H but are otherwise as previously defined and each of $R^1$, $R^4$, $R^5$ and $R^6$ is as previously defined, can be prepared from compounds according to formula (Id) where $R^2$ does not represent H but is otherwise as previously defined, $R^3$ represents H, and each of $R^1$, $R^4$, $R^5$ and $R^6$ is as previously defined, as in step a, using a base such as sodium hydride and a solvent such as THF, followed by reaction with an electrophilic reagent such as methoxy or other alkyl electrophile.

Scheme VII

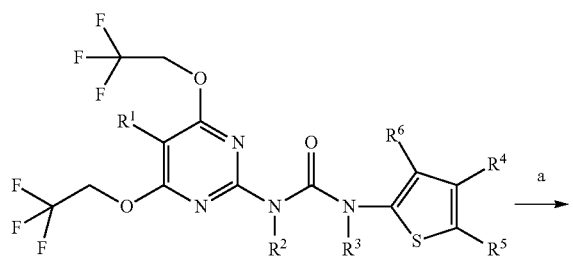

(Ic)

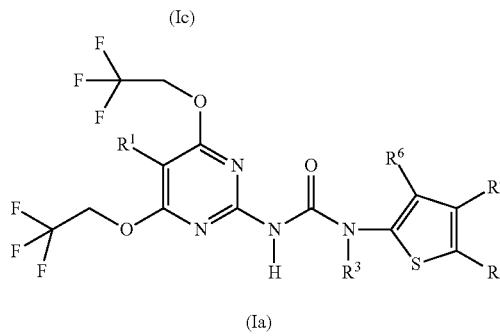

(Ia)

In Scheme VII above, compounds according to formula (Ia) where $R^2$ represents H, $R^3$ does not represent H but is otherwise as previously defined and each of $R^1$, $R^4$, $R^5$ and $R^6$ is as previously defined, can be prepared from compounds according to formula (Ic) where $R^2$ and $R^3$ do not represent H but are as otherwise previously defined and each of $R^1$, $R^4$, $R^5$ and $R^6$ is as previously defined, as in step a, by removal of $R^2$ when $R^2$ is such a group that can be removed without removal of $R^3$ (for example see: Protecting Groups in Organic Synthesis, Third Edition, T. W. Greene and P. G. M. Wuts, John Wiley and Sons, Inc., 1999).

Example 1

Preparation of tert-butyl 5-(trifluoromethyl)thiophen-2-ylcarbamate

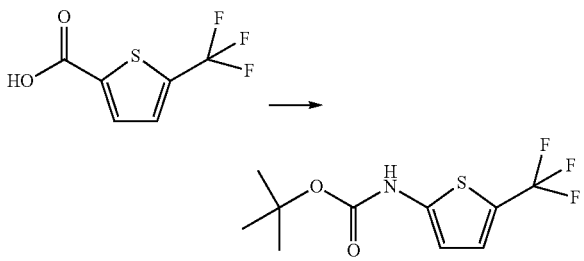 [SMILES: O=C(O)c1ccc(C(F)(F)F)s1 ; CC(C)(C)OC(=O)Nc1ccc(C(F)(F)F)s1]

To 5-(trifluoromethyl)thiophene-2-carboxylic acid in tBuOH (50 mL) was added triethylamine (1.53 mL, 11 mmol) and diphenylphosphoryl azide (DPPA) (2.4 mL, 11 mmol). This mixture was heated to 90° C., and was stirred overnight (ca. 16 hours). Thin layer chromatography (TLC) indicated that the reaction was complete. The solvent was removed under reduced pressure, the residue was dissolved in ethyl acetate (EtOAc) and washed 1× with NaHCO$_3$ aq sat, 1× with citric acid (10% aqueous), and 1× brine. The solution was dried over MgSO$_4$, filtered and concentrated. After silica gel chromatography (5 to 20% EtOAc/hexanes) the title compound was afforded (1.46 g, 44% over 3 steps) as a yellow/orange solid, mp 118-120° C.; R$_f$=0.31 (10% EtOAc/hex); $^1$H NMR (DMSO-d$_6$) δ 11.03 (br s, 1H), 7.38 (app d, 1H, J=4.1 Hz), 6.51 (app d, 1H, J=3.3 Hz), 1.49 (s, 9H); GCMS (EI) m/z 267 (M$^+$).

Example 2

Preparation of N-Methyl-5-(trifluoromethyl)thiophen-2-amine

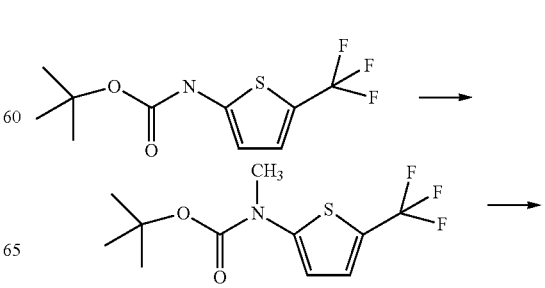

-continued

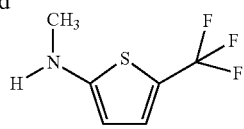

To tert-butyl 5-(trifluoromethyl)thiophen-2-ylcarbamate (0.40 g, 1.5 mmol) in DMF (9 mL) at 0° C. was added NaH (72 mg, 1.8 mmol, 60% dispersion in mineral oil) in one portion. After 40 minutes MeI (0.20 mL, 1.8 mmol) was added via syringe. After stirring for 30 minutes at 0° C., TLC of a quenched aliquot showed the reaction was complete. The reaction was quenched by pouring into a biphasic mixture of 1N HCl and EtOAc. The layers were separated, and the organic layer was washed 3× with H₂O, 1× with brine, dried over MgSO₄, filtered, and concentrated under reduced pressure to afford a yellow oil. The crude oil was added to CH₂Cl₂ (2 mL) and trifluoroacetic acid (2 mL). After this mixture had been stirred at ambient temperature for 80 minutes, TLC showed the reaction was complete. The solvents were removed under reduced pressure and the residue was taken up in CH₂Cl₂ and was washed with NaHCO₃ aq sat. This aqueous wash was back extracted 1× with CH₂Cl₂, then the combined organic layers were dried over MgSO₄, filtered, and concentrated under reduced pressure. N-Methyl-5-(trifluoromethyl)thiophen-2-amine was used directly in the next step.

Example 3

Preparation of 5-methylthiophen-2-amine hydrochloride

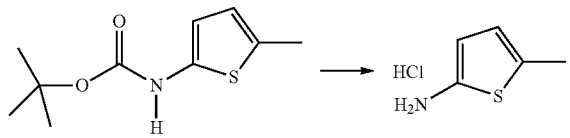

To a solution of an N-Boc protected 5-methylthiophen-2-amine compound (0.5 g, 2.35 mmol) in 1,4-dioxane (5 mL) was added HCl in 1,4-dioxane (5 mL) at 0° C. and the mixture was stirred at room temperature for 16 hours. The solvent was evaporated under reduced pressure and the residue obtained was washed with Et₂O to give the title compound (25 g, 71.4%).

Example 4

Preparation of 3-(4,6-bis(2,2,2-trifluoroethoxy)pyrimidin-2-yl)-1-methyl-1-(5-(trifluoroethyl)thiophen-2-yl)urea (2)

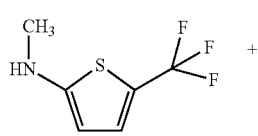 +

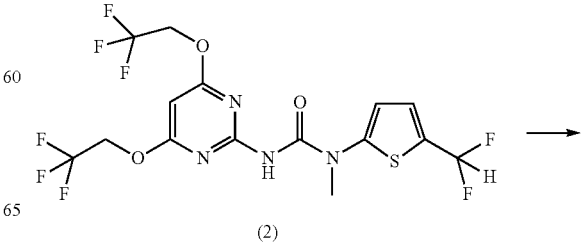

To a solution of N-methyl-5-(trifluoromethyl)thiophen-2-amine in CH₂Cl₂ (2 mL) was added 2-isocyanato-4,6-bis(2,2,2-trifluoroethoxy)pyrimidine (1.6 mL, 1.0 M in THF) (prepared as described in U.S. Pat. No. 8,013,154, the contents of which were incorporated herein above by reference in their entirety). This reaction was stirred at ambient temperature overnight. TLC indicated the reaction was complete. The solvent was removed under reduced pressure and the residue was purified using normal phase chromatography which afforded product (471 mg, 56% over three steps) as an off-white solid, mp 99-101° C.: $R_f$=0.26 (30% EtOAc, hex); $^1$H NMR (DMSO-d₆) 10.34 (s, 1H), 7.48 (d, 1H, J=3.3 Hz), 6.78 (d, 1H, J=4.3 Hz), 6.28 (s, 1H), 5.02 (q, 4H, J=17.8, 8.9 Hz), 3.49 (s, 3H); ESIMS m/z 497 [(M−1)+].

Example 5

Preparation of 3-methyl-3-(4,6-bis(2,2,2-trifluoroethoxy)pyrimidin-2-yl)-1-methyl-1-(5-(trifluoromethyl)thiophen-2-yl)urea (6)

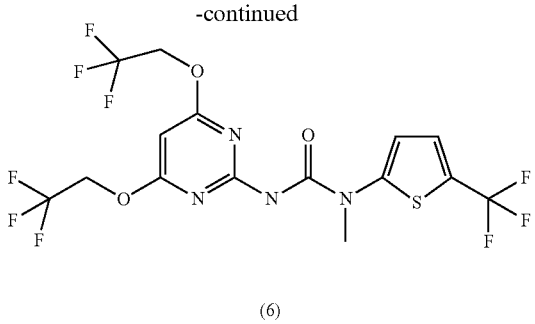

(6)

To a suspension of NaH (18 mg, 0.36 mmol) in anhydrous THF (3 mL) was added a solution of the 3-(4,6-bis(2,2,2-trifluoroethoxy)pyrimidin-2-yl)-1-methyl-1-(5-(trifluoromethyl)thiophen-2-yl)urea (2) (150 mg, 0.30 mmol). The reaction was stirred for 10 minutes after which time gas evolution had subsided. To the reaction was added methyl iodide (51.2 mg, 0.36 mmol). The reaction was stirred at ambient temperature for 2 h. The reaction was quenched with H$_2$O (5 mL) and extracted with t-butyl ethyl ether (3×5 mL). The organics were combined and extracted with an equal amount of H$_2$O. The organics were dried (MgSO$_4$), filtered and concentrated to afford crude product. The crude material was purified by silica gel chromatography (5% EtOAc in pet ether) to afford 3-methyl-3-(4,6-bis(2,2,2-trifluoroethoxy)pyrimidin-2-yl)-1-methyl-1-(5-(trifluoromethyl)thiophen-2-yl)urea (6) as an off white solid (31 mg, 20%), mp 113-114° C.; $^1$H NMR (400 MHz, Acetone-d$_6$) δ 7.35-7.24 (m, 1H), 6.73 (d, J=4.2 Hz, 1H), 5.88 (s, 1H), 4.76 (q, J=8.7 Hz, 4H), 3.35 (s, 3H), 3.28 (s, 3H); ESIMS m/z 513 ([M+H]+).

Example 6

Preparation of 3-(methoxymethyl)-3-(4,6-bis(2,2,2-trifluoroethoxy)pyrimidin-2-yl)-1-(5-(trifluoromethyl)thiophen-2-yl)urea (4)

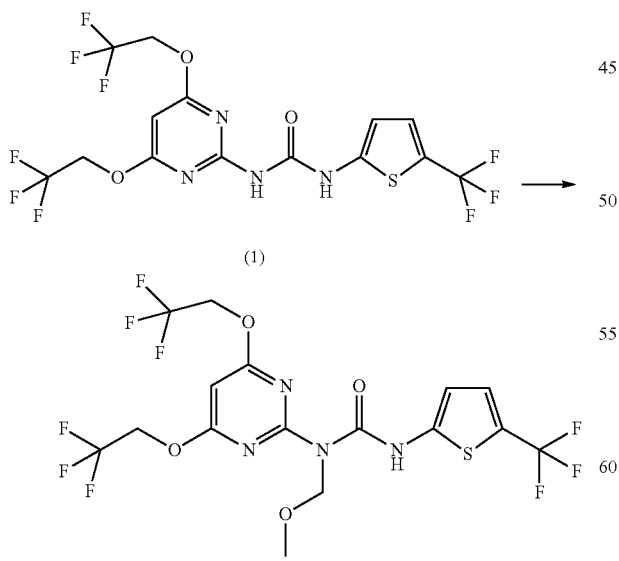

To a solution of 3-(4,6-bis(2,2,2-trifluoroethoxy)pyrimidin-2-yl)-1-(5-(trifluoromethyl)thiophen-2-yl)urea (1) (150 mg, 0.31 mmol) in anhydrous dimethyl formamide (DMF, 1.5 mL) at ambient temperature was added NaH (6.6 mg, 0.28 mmol, 60% dispersion in mineral oil). After stirring 20 minutes a solution of bromomethyl methyl ether (35 mg, 0.28 mmol) in anhydrous DMF (0.5 mL) was added. After 2.5 h the reaction was judged complete by TLC analysis. To the reaction was carefully added H$_2$O (2 mL). The reaction was extracted with EtOAc (10 mL). The EtOAc solution was washed with H$_2$O (3×7 mL) followed by brine (7 mL). The organics were dried (Na$_2$SO$_4$), filtered and evaporated to give crude product. The crude material was purified by silica gel chromatography (0 to 8% EtOAc in pet ether) to afford 3-(methoxymethyl)-3-(4,6-bis(2,2,2-trifluoroethoxy)pyrimidin-2-yl)-1-(5-(trifluoromethyl)thiophen-2-yl)urea (4) as an off white solid (18 mg, 11%), mp 118-119° C.; $^1$H NMR (400 MHz, Acetone-d$_6$) δ 11.84 (s, 1H), 7.41-7.28 (m, 1H), 6.66 (dd, J=4.1, 0.9 Hz, 1H), 6.18 (s, 1H), 5.54 (s, 2H), 5.02 (q, J=8.6 Hz, 4H), 3.27 (s, 3H); ESIMS m/z 527 ([M–H]+).

Example 7

Preparation of 3-(benzyloxymethyl)-3-(4,6-bis(2,2,2-trifluoroethoxy)pyrimidin-2-yl)-1-(methoxymethyl)-1-(5-trifluoromethyl)thiophen-2-yl)urea (10)

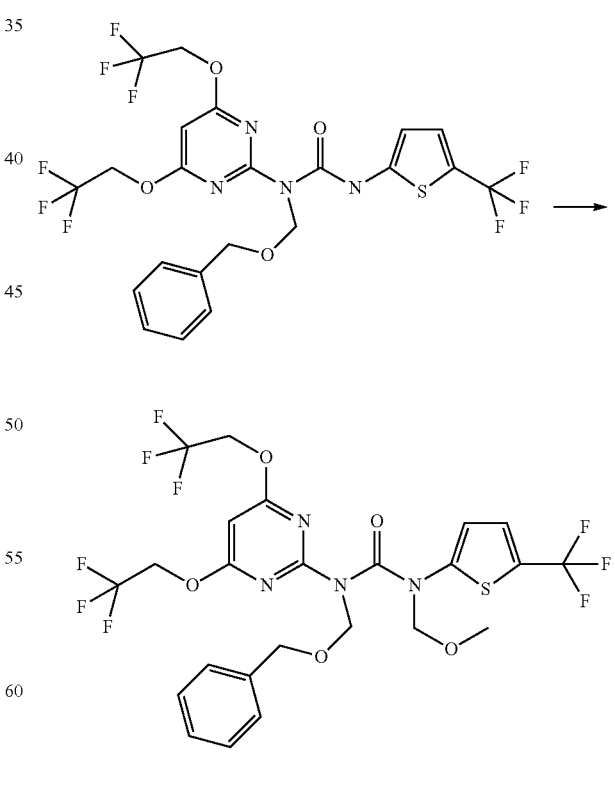

To a solution of 3-(benzyloxymethyl)-3-(4,6-bis(2,2,2-trifluoroethoxy)pyrimidin-2-yl)-1-(5-(trifluoromethyl)thiophen-2-yl)urea (250 mg, 0.41 mmol) in anhydrous DMF (2.5 mL), with an internal temperature of ≤−10° C., was slowly added NaH (20 mg, 0.5 mmol, 60% dispersion in mineral oil). The mixture was stirred 30 minutes resulting in a clear yellow solution. To this solution was slowly added a solution of bromomethyl methyl ether (51.6 mg, 0.41 mmol) in anhydrous DMF (0.5 mL). After 2.5 h the reaction was quenched with ice and diluted with EtOAc (25 mL). The mixture was extracted with $H_2O$ (3×15 mL) and brine (15 mL). The EtOAc solution was dried ($Na_2SO_4$), filtered and evaporated to give crude product. The crude product was purified by silica gel chromatography (2 to 6% EtOAc in pet ether) to afford the product as a pale yellow gum (185 mg, 69%). $^1$H NMR (400 MHz, Acetone-$d_6$) δ 7.29-7.08 (m, 6H), 6.82 (d, J=3.9 Hz, 1H), 5.90 (s, 1H), 5.40 (s, 2H), 5.10 (s, 2H), 4.79 (q, J=8.7 Hz, 4H), 4.69 (s, 2H), 3.27 (s, 3H); ESIMS m/z 649 ([M+H]+).

Example 8

Preparation of 3-(benzyloxymethyl)-3-(4,6-bis(2,2,2-trifluoroethoxy)pyrimidin-2-yl)-1-(5-(trifluoromethyl)thiophen-2-yl)urea

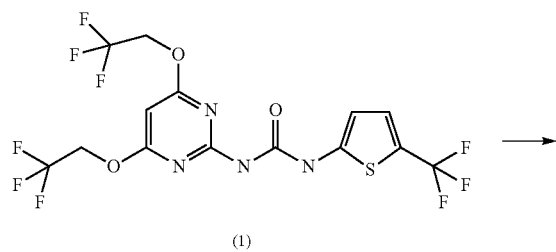

(1)

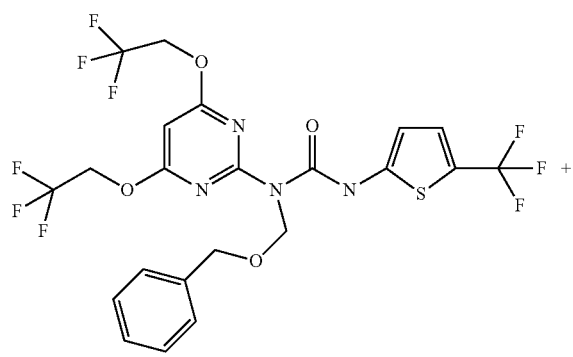

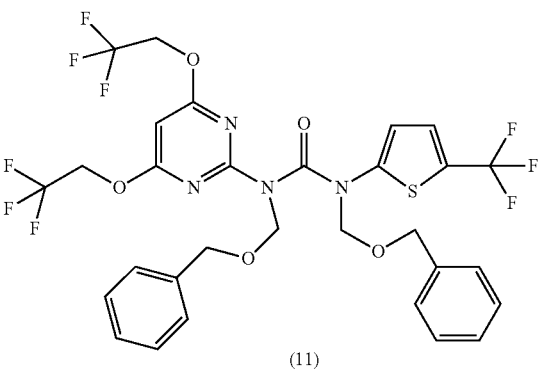

(11)

To a solution of 3-(4,6-bis(2,2,2-trifluoroethoxy)pyrimidin-2-yl)-1-(5-(trifluoromethyl)thiophen-2-yl)urea (1) (750 mg, 1.54 mmol) in anhydrous DMF (7.5 mL) at ambient temperature was added NaH (37 mg, 1.54 mmol, 60% dispersion in mineral oil). After stirring for 20 minutes a solution of benzyloxymethylchloride (241 mg, 1.54 mmol) in anhydrous DMF (0.75 mL) was added. After 2 h of stirring at room temperature the reaction was quenched with $H_2O$ (5 mL) and diluted with EtOAc. The organic layer was separated and washed with $H_2O$ (3×10 mL) and brine (10 mL). The organics were dried ($Na_2SO_4$), filtered and evaporated. The crude material was purified by silica gel chromatography (0 to 10% EtOAc in pet ether) to afford 3-(benzyloxymethyl)-3-(4,6-bis(2,2,2-trifluoroethoxy)pyrimidin-2-yl)-1-(5-(trifluoromethyl)thiophen-2-yl)urea as an off white solid (550 mg, 59%), mp 101-104° C.; $^1$H NMR (400 MHz, Acetone-$d_6$) δ 11.82 (s, 1H), 7.37-6.99 (m, 5H), 6.65 (d, J=4.0 Hz, 1H), 6.17 (s, 1H), 5.71 (s, 2H), 4.97 (q, J=8.5 Hz, 4H), 4.60 (s, 2H); ESIMS m/z 605 ([M+H]+). Also isolated was a by-product 1,3-bis(benzyloxymethyl)-3-(4,6-bis(2,2,2-trifluoroethoxy)pyrimidin-2-yl)-1-(5-(trifluoromethyl)thiophen-2-yl)urea (11) as a pale yellow gum (65 mg); $^1$H NMR (400 MHz, Aceton) δ 7.29-7.05 (m, 10H), 6.87 (d, J=4.0 Hz, 1H), 5.90 (s, 1H), 5.40 (s, 2H), 5.23 (s, 2H), 4.75 (q, J=8.7 Hz, 4H), 4.69 (s, 2H), 4.52 (s, 2H); ESIMS m/z 618 ([M-PhCH2O]+).

Compounds 1-45 identified in Table 1 were prepared in Examples 4-8, utilizing reactions similar to those described in one or more of Examples 1-8, and/or in accordance with one or more of Schemes I-VII. Table 1 also identifies precursor or starting compounds used in preparation of Compounds 1-45. The precursor or starting amines identified in connection with Compounds 20-45 were prepared as shown in Scheme I (step a or steps a and b) to provide a carbamate which was deprotected in accordance with step a of Scheme II or III. Example 3 also provides an exemplary deprotection reaction. The Cl analog illustrated in connection with Compounds 20, 29 and 43 resulted from exchange of Cl for Br during the deprotection reaction. In Compound 21, complete exchange of Cl for Br occurred resulting only in the Cl compound.

TABLE 1

| Compound No. | Structure | Precursor |
|---|---|---|
| 1 | 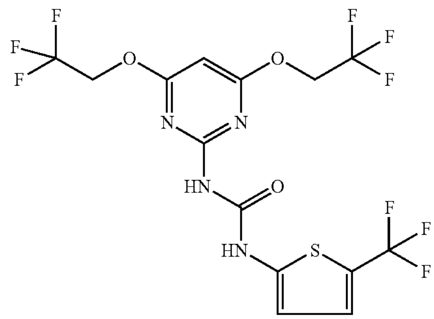 [SMILES: O=C(Nc1nc(OCC(F)(F)F)cc(OCC(F)(F)F)n1)Nc1ccc(C(F)(F)F)s1] | trifluoromethyl thiophen-2-amine |
| 2 | 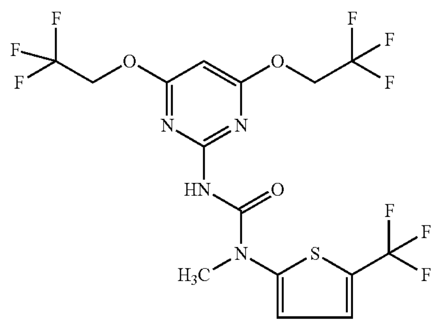 [SMILES: CN(C(=O)Nc1nc(OCC(F)(F)F)cc(OCC(F)(F)F)n1)c1ccc(C(F)(F)F)s1] | N-Methyl-5-(trifluoromethyl)-thiophen-2-amine |
| 3 | 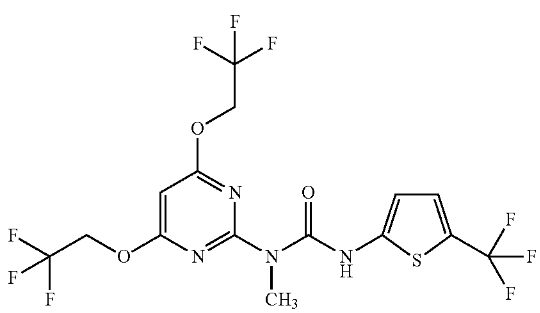 [SMILES: CN(C(=O)Nc1ccc(C(F)(F)F)s1)c1nc(OCC(F)(F)F)cc(OCC(F)(F)F)n1] | Compound 1, methyl iodide |
| 4 | 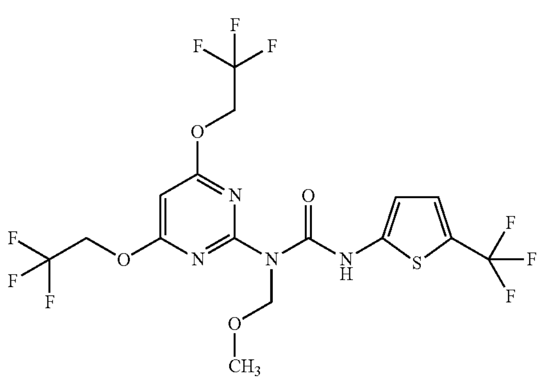 [SMILES: COCN(C(=O)Nc1ccc(C(F)(F)F)s1)c1nc(OCC(F)(F)F)cc(OCC(F)(F)F)n1] | Compound 1, bromomethyl methyl ether |

TABLE 1-continued
| Compound No. | Structure | Precursor |
|---|---|---|
| 5 | 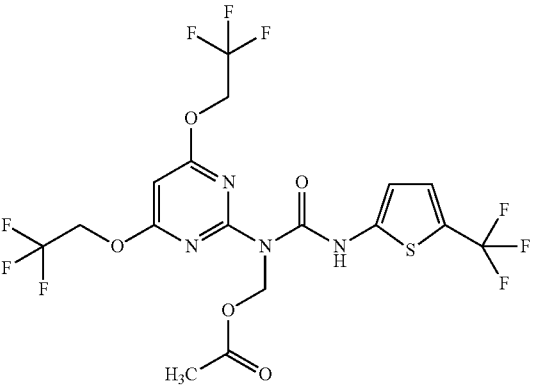 [SMILES: CC(=O)OCN(C(=O)Nc1ccc(C(F)(F)F)s1)c1nc(OCC(F)(F)F)cc(OCC(F)(F)F)n1] | Compound 1, chloromethyl acetate |
| 6 | 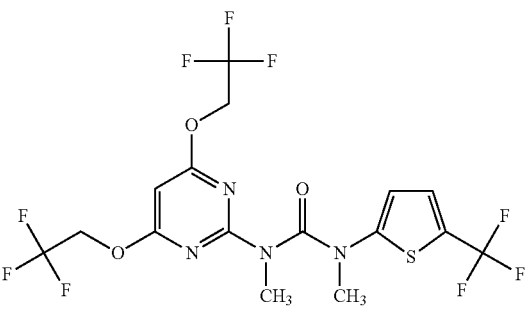 [SMILES: CN(C(=O)N(C)c1ccc(C(F)(F)F)s1)c1nc(OCC(F)(F)F)cc(OCC(F)(F)F)n1] | Compound 2, methyl iodide |
| 7 | 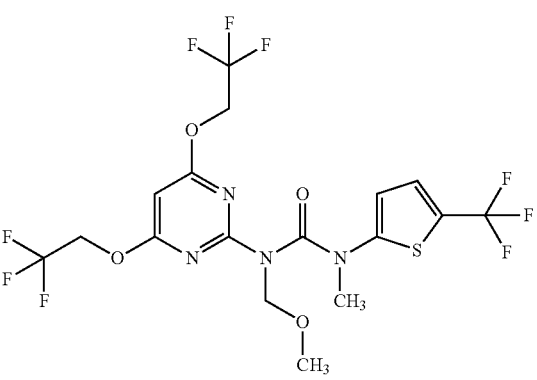 [SMILES: COCN(C(=O)N(C)c1ccc(C(F)(F)F)s1)c1nc(OCC(F)(F)F)cc(OCC(F)(F)F)n1] | Compound 2, bromomethyl methyl ether |
| 8 | 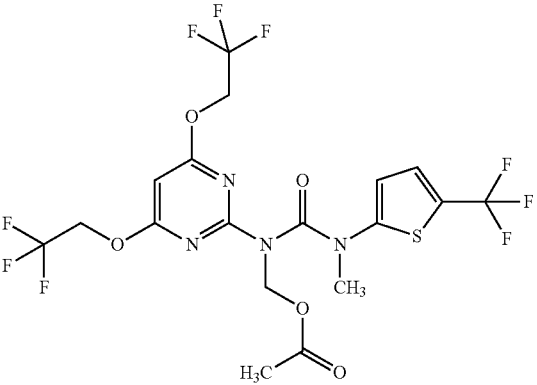 [SMILES: CC(=O)OCN(C(=O)N(C)c1ccc(C(F)(F)F)s1)c1nc(OCC(F)(F)F)cc(OCC(F)(F)F)n1] | Compound 2, chloromethyl acetate |

TABLE 1-continued
| Compound No. | Structure | Precursor |
|---|---|---|
| 9 | 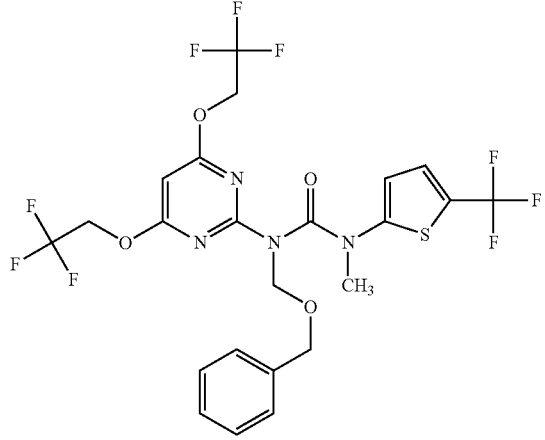 [SMILES: CN(C(=O)N(COCc1ccccc1)c1nc(OCC(F)(F)F)cc(OCC(F)(F)F)n1)c1ccc(C(F)(F)F)s1] | Compound 2, benzyl bromo methyl ether |
| 10 | 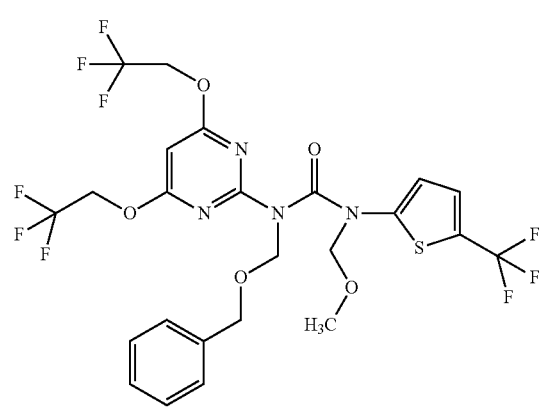 [SMILES: COCN(C(=O)N(COCc1ccccc1)c1nc(OCC(F)(F)F)cc(OCC(F)(F)F)n1)c1ccc(C(F)(F)F)s1] | Refer to Examples 7 and 8 |
| 11 | 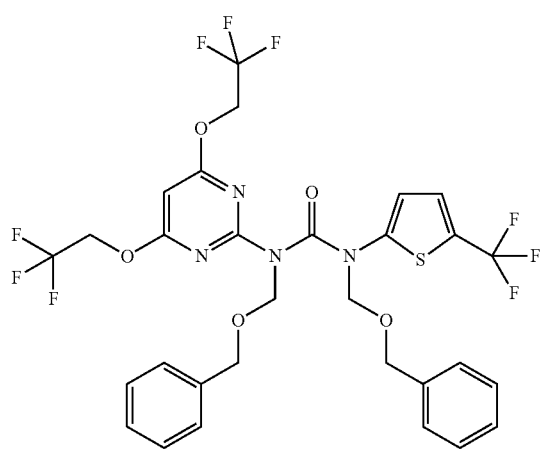 [SMILES: O=C(N(COCc1ccccc1)c1nc(OCC(F)(F)F)cc(OCC(F)(F)F)n1)N(COCc1ccccc1)c1ccc(C(F)(F)F)s1] | Compound 1, benzyl bromo methyl ether |
| 12 | 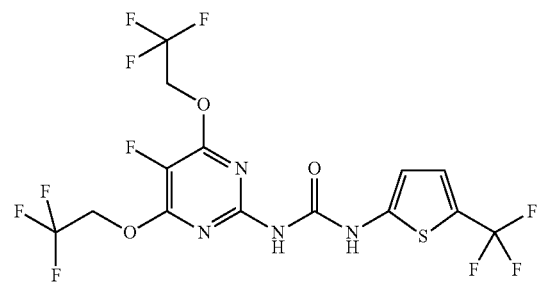 [SMILES: O=C(Nc1nc(OCC(F)(F)F)c(F)c(OCC(F)(F)F)n1)Nc1ccc(C(F)(F)F)s1] | 5-fluoro-2-isocyanato-4,6-bis(2,2,2-trifluoroethoxy)-pyrimidine, trifluoromethyl thiophene-2amine |

TABLE 1-continued

| Compound No. | Structure | Precursor |
|---|---|---|
| 13 | 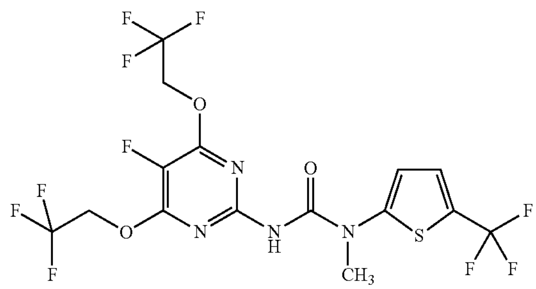 [SMILES: CN(C(=O)Nc1nc(OCC(F)(F)F)c(F)c(OCC(F)(F)F)n1)c1ccc(C(F)(F)F)s1] | 5-fluoro-2-isocyanato-4,6-bis(2,2,2-trifluoroethoxy)-pyrimidine |
| 14 | 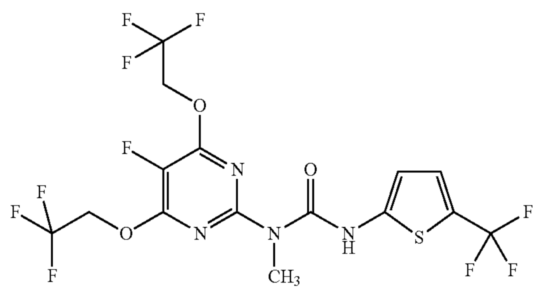 [SMILES: CN(C(=O)Nc1ccc(C(F)(F)F)s1)c1nc(OCC(F)(F)F)c(F)c(OCC(F)(F)F)n1] | Compound 12, methyl iodide |
| 15 | 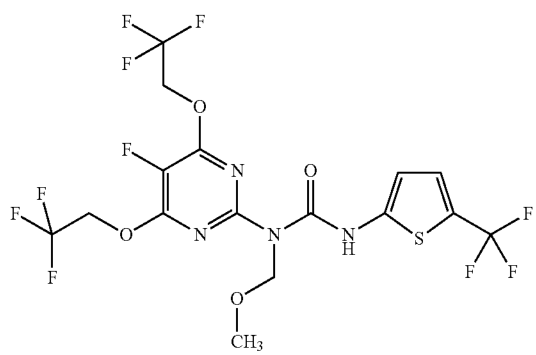 [SMILES: COCN(C(=O)Nc1ccc(C(F)(F)F)s1)c1nc(OCC(F)(F)F)c(F)c(OCC(F)(F)F)n1] | Compound 12, bromomethyl methyl ether |
| 16 | 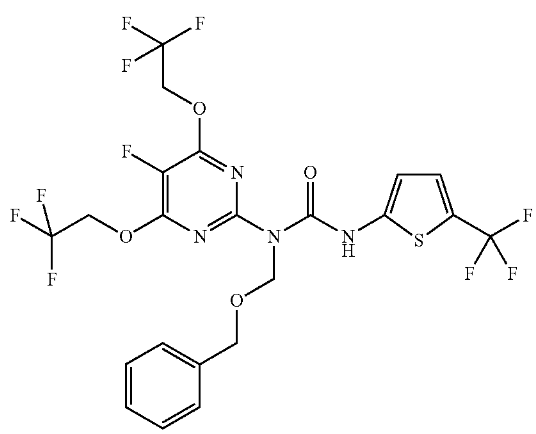 [SMILES: O=C(Nc1ccc(C(F)(F)F)s1)N(COCc1ccccc1)c1nc(OCC(F)(F)F)c(F)c(OCC(F)(F)F)n1] | Compound 12, benzyl bromo methyl ether |

TABLE 1-continued

| Compound No. | Structure | Precursor |
|---|---|---|
| 17 | 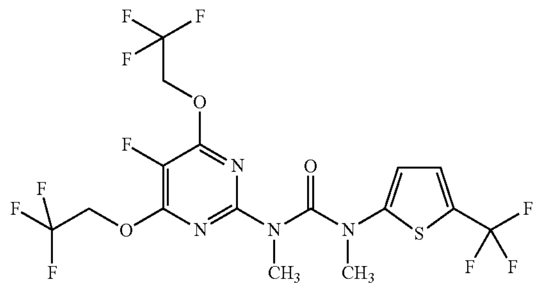 [SMILES: CN(C(=O)N(C)c1ccc(C(F)(F)F)s1)c1nc(OCC(F)(F)F)c(F)c(OCC(F)(F)F)n1] | Compound 13, methyl iodide |
| 18 | 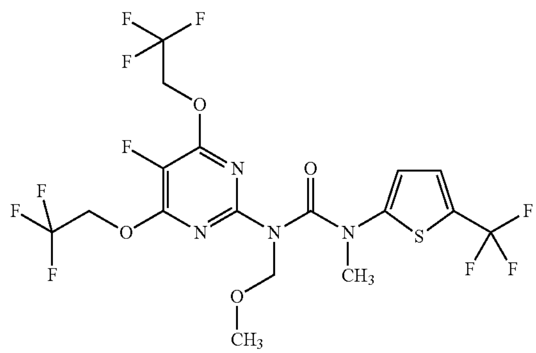 [SMILES: COCN(C(=O)N(C)c1ccc(C(F)(F)F)s1)c1nc(OCC(F)(F)F)c(F)c(OCC(F)(F)F)n1] | Compound 13, bromomethyl methyl ether |
| 19 | 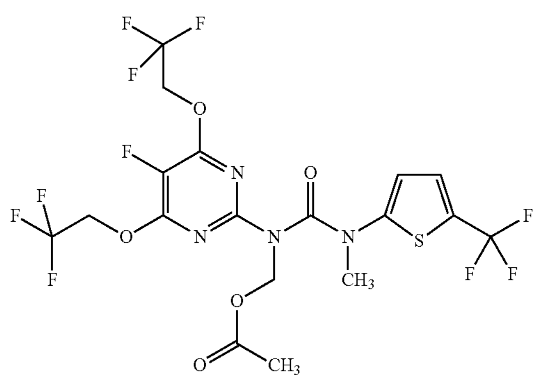 [SMILES: CC(=O)OCN(C(=O)N(C)c1ccc(C(F)(F)F)s1)c1nc(OCC(F)(F)F)c(F)c(OCC(F)(F)F)n1] | Compound 13, chloromethyl acetyl |
| 20 | 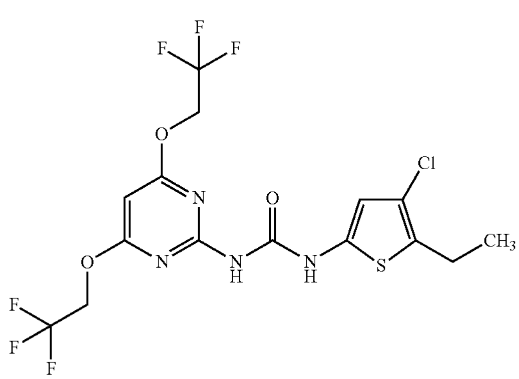 [SMILES: CCc1sc(NC(=O)Nc2nc(OCC(F)(F)F)cc(OCC(F)(F)F)n2)cc1Cl] | 4-bromo-5-ethyl-thiophen-2-amine |

TABLE 1-continued
| Compound No. | Structure | Precursor |
|---|---|---|
| 21 | 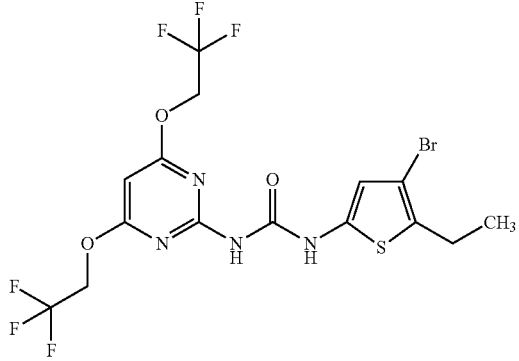 [SMILES: CCc1sc(NC(=O)Nc2nc(OCC(F)(F)F)cc(OCC(F)(F)F)n2)cc1Br] | 4-bromo-5-ethyl-N-methyl-thiophen-2-amine |
| 22 | 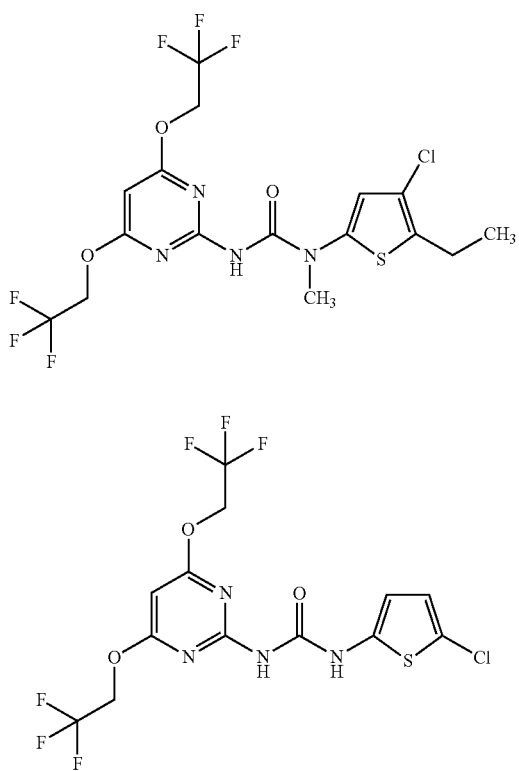 | 5-chlorothiophen-2-amine |
| 23 | 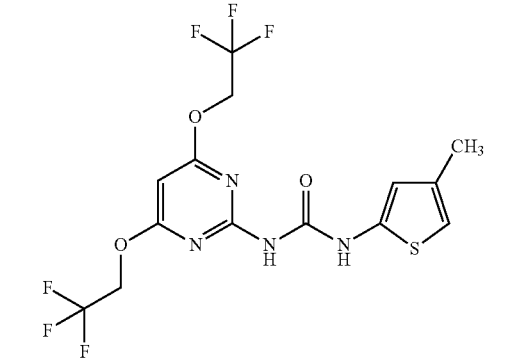 [SMILES: Cc1csc(NC(=O)Nc2nc(OCC(F)(F)F)cc(OCC(F)(F)F)n2)c1] | metrhylthiophen-2-amine |

TABLE 1-continued

| Compound No. | Structure | Precursor |
|---|---|---|
| 24 | 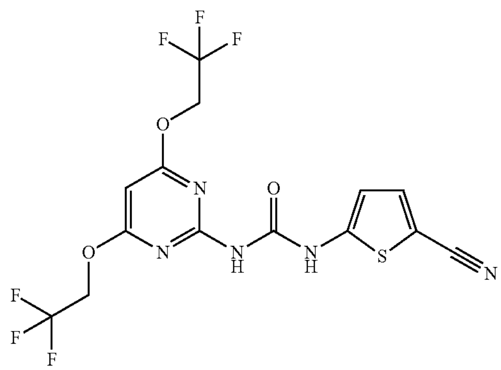 [SMILES: N#Cc1ccc(NC(=O)Nc2nc(OCC(F)(F)F)cc(OCC(F)(F)F)n2)s1] | 5-cyanothiophen-2-amine |
| 25 | 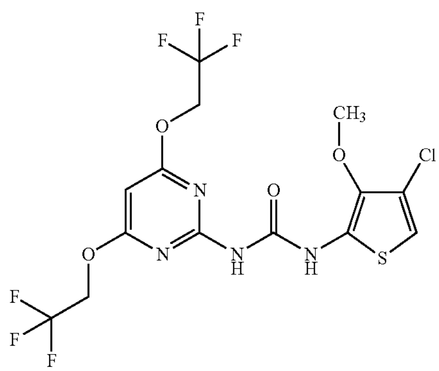 [SMILES: COc1c(Cl)csc1NC(=O)Nc1nc(OCC(F)(F)F)cc(OCC(F)(F)F)n1] | 4-chloro-3-methoxy-thiophen-2-amine |
| 26 | 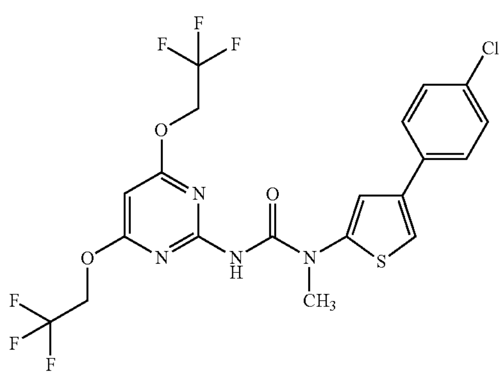 [SMILES: CN(C(=O)Nc1nc(OCC(F)(F)F)cc(OCC(F)(F)F)n1)c1cc(-c2ccc(Cl)cc2)cs1] | 4-(4-chlorophenyl)-N-methylthiophene-2-amine |
| 27 | 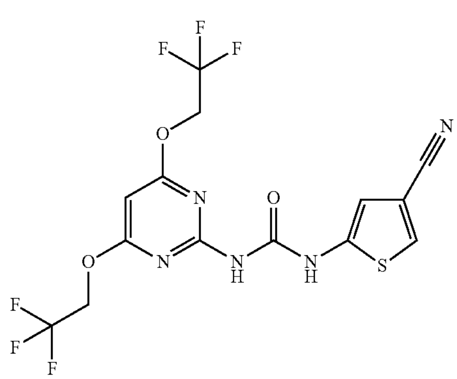 [SMILES: N#Cc1csc(NC(=O)Nc2nc(OCC(F)(F)F)cc(OCC(F)(F)F)n2)c1] | 4-cyanothiophene-2-amine |

TABLE 1-continued

| Compound No. | Structure | Precursor |
|---|---|---|
| 28 | 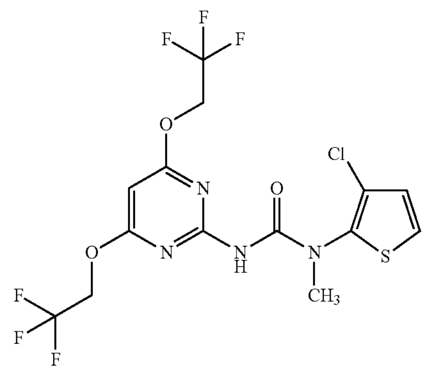 [SMILES: CN(C(=O)Nc1nc(OCC(F)(F)F)cc(OCC(F)(F)F)n1)c1sccc1Cl] | 3-chloro-N-methylthiophene-2-amine |
| 29 | 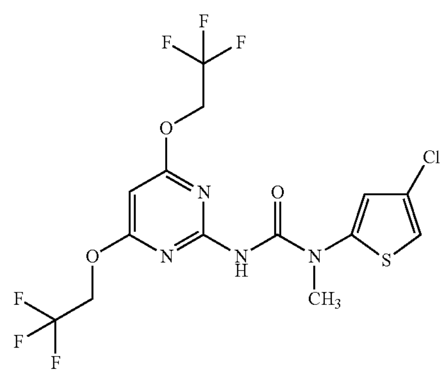 [SMILES: CN(C(=O)Nc1nc(OCC(F)(F)F)cc(OCC(F)(F)F)n1)c1cc(Cl)cs1] | 3-bromo-N-methylthiophene-2-amine |
| | | |
| 30 | 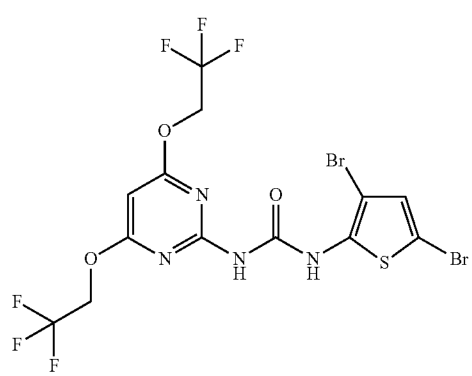 [SMILES: O=C(Nc1nc(OCC(F)(F)F)cc(OCC(F)(F)F)n1)Nc1sc(Br)cc1Br] | 3,5-dibromothiophene-2-amine |

TABLE 1-continued

| Compound No. | Structure | Precursor |
|---|---|---|
| 31 | 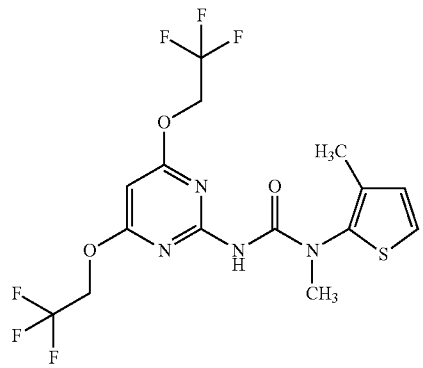 [SMILES: Cc1ccsc1N(C)C(=O)Nc1nc(OCC(F)(F)F)cc(OCC(F)(F)F)n1] | 3-methyl-N-methylthiophene-2-amine |
| 32 | 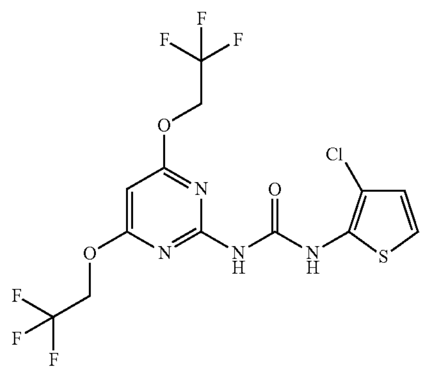 [SMILES: O=C(Nc1nc(OCC(F)(F)F)cc(OCC(F)(F)F)n1)Nc1sccc1Cl] | 3-chlorothiophene-2-amine |
| 33 | 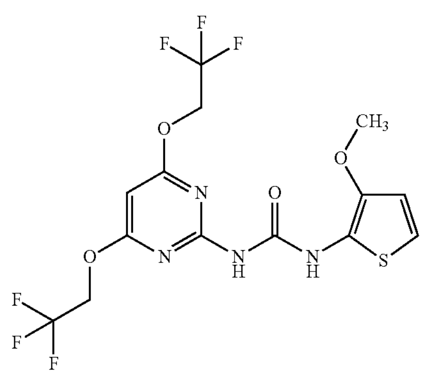 [SMILES: COc1ccsc1NC(=O)Nc1nc(OCC(F)(F)F)cc(OCC(F)(F)F)n1] | 3-methoxythiophene-2-amine |
| 34 | 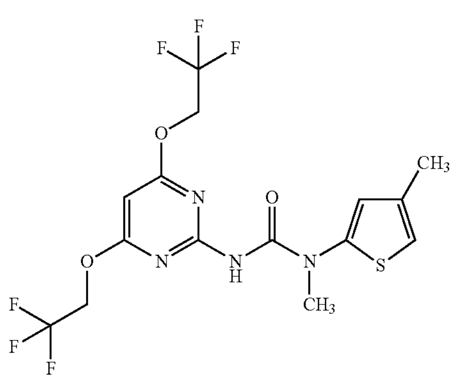 [SMILES: Cc1csc(N(C)C(=O)Nc2nc(OCC(F)(F)F)cc(OCC(F)(F)F)n2)c1] | 4-methyl-N-methylthiophene-2-amine |

TABLE 1-continued

| Compound No. | Structure | Precursor |
|---|---|---|
| 35 | 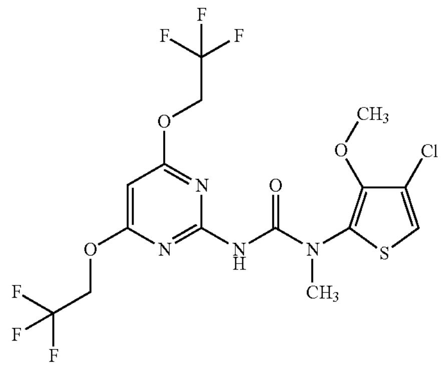 [SMILES: COc1c(Cl)csc1N(C)C(=O)Nc1nc(OCC(F)(F)F)cc(OCC(F)(F)F)n1] | 4-chloro-3-methoxy-N-methylthiophene-2-amine |
| 36 | 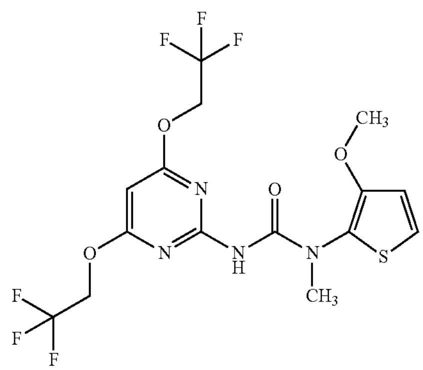 [SMILES: COc1ccsc1N(C)C(=O)Nc1nc(OCC(F)(F)F)cc(OCC(F)(F)F)n1] | 3-methoxy-N-methylthiophene-2-amine |
| 37 | 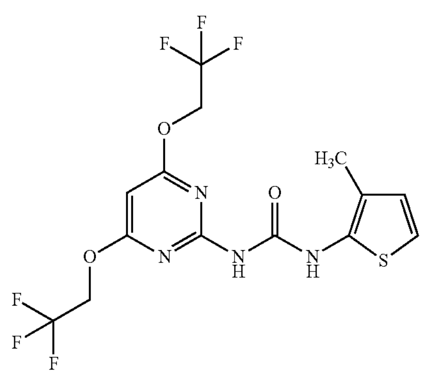 [SMILES: Cc1ccsc1NC(=O)Nc1nc(OCC(F)(F)F)cc(OCC(F)(F)F)n1] | 3-methylthiophene-2-amine |
| 38 | 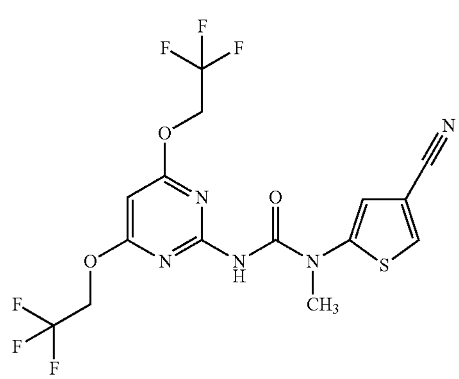 [SMILES: CN(C(=O)Nc1nc(OCC(F)(F)F)cc(OCC(F)(F)F)n1)c1cc(C#N)cs1] | 4-cyano-N-methylthiophene-2-amine |

TABLE 1-continued

| Compound No. | Structure | Precursor |
|---|---|---|
| 39 | 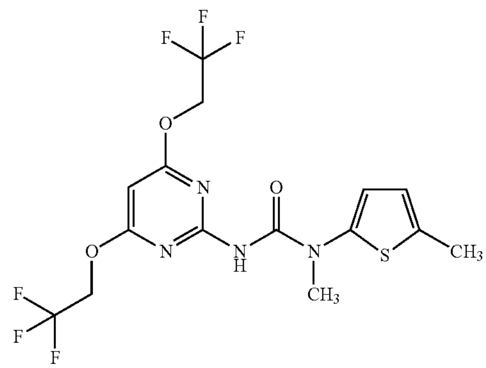 [SMILES: Cc1ccc(N(C)C(=O)Nc2nc(OCC(F)(F)F)cc(OCC(F)(F)F)n2)s1] | 5-methyl-N-methylthiophene-2-amine |
| 40 | 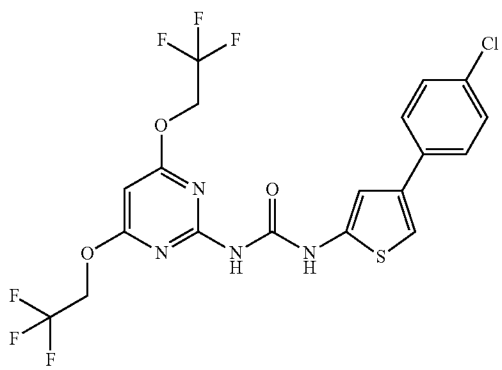 [SMILES: O=C(Nc1nc(OCC(F)(F)F)cc(OCC(F)(F)F)n1)Nc1cc(-c2ccc(Cl)cc2)cs1] | 4-(4-chlorophenyl)-thiophene-2-amine |
| 41 | 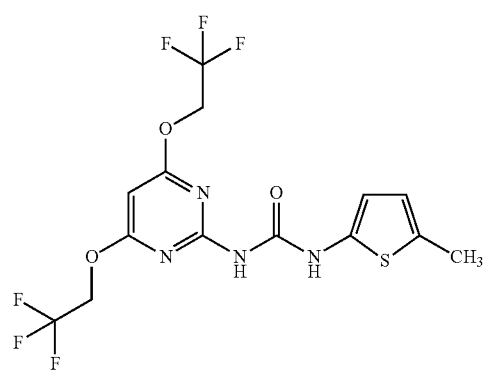 [SMILES: Cc1ccc(NC(=O)Nc2nc(OCC(F)(F)F)cc(OCC(F)(F)F)n2)s1] | 5-methylthiophene-2-amine |
| 42 | 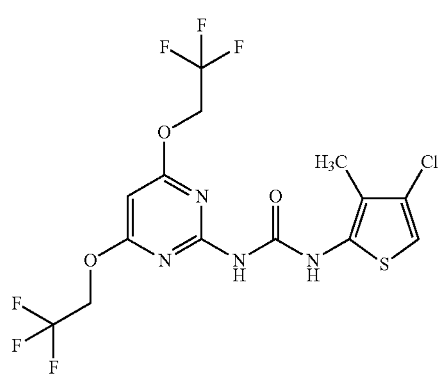 [SMILES: Cc1c(Cl)csc1NC(=O)Nc1nc(OCC(F)(F)F)cc(OCC(F)(F)F)n1] | 4-chloro-3-methylthiophene-2-amine |

TABLE 1-continued
| Compound No. | Structure | Precursor |
|---|---|---|
| 43 | 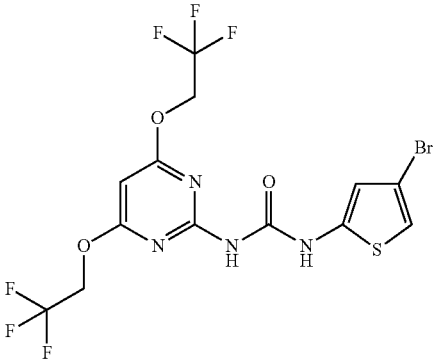 [SMILES: O=C(Nc1nc(OCC(F)(F)F)cc(OCC(F)(F)F)n1)Nc1cc(Br)cs1] | 4-bromothiophene-2-amine |
| 44 | 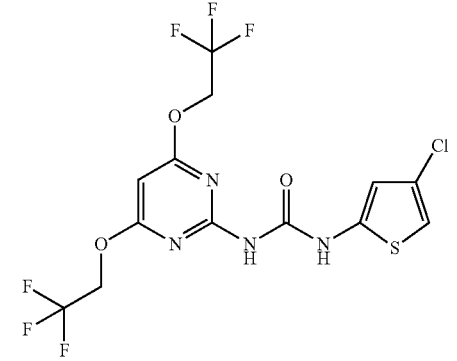 [SMILES: O=C(Nc1nc(OCC(F)(F)F)cc(OCC(F)(F)F)n1)Nc1cc(Cl)cs1] | 3,4,5-trichlorothiophene-2-amine |
| 45 | 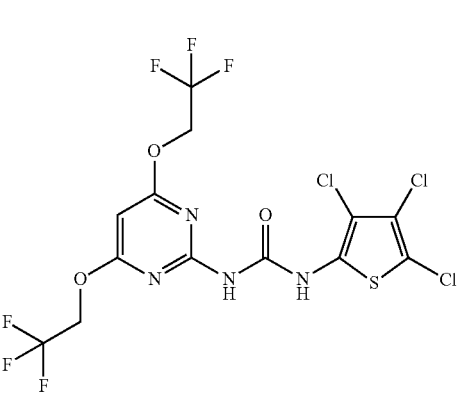 | 3-bromothiophene-2-amine |

Table 2 provides analytical data associated with Compounds 1-45.

TABLE 2

| NO. | Appearance | MP (°C.) | IR (cm$^{-1}$) | MASS | NMR |
|---|---|---|---|---|---|
| 1 | White Solid | 172-174 | | ESIMS m/z 485.3 ([M + H]$^+$), 483.1 ([M − H]$^-$) | $^1$H NMR (DMSO-d$_6$) δ 11.27 (s, 1H), 10.70 (s, 1H), 7.52 (dd, J = 4.1, 1.4 Hz, 1H), 6.72 (d, J = 4.1 Hz, 1H), 6.35 (s, 1H), 5.17 (q, J = 17.6, 8.8 Hz, 4H). |
| 2 | Off-White Solid | 99-101 | | ESIMS m/z 499.3 ([M + H]$^+$), 496.8 ([M − H]$^-$) | $^1$H NMR (DMSO-d$_6$) δ 10.35 (s, 1H), 7.49 (d, J = 3.3 Hz 1H), 6.78 (d, J = 4.3 Hz, 1H), 6.29 (s, 1H), 5.00 (q, J = 17.8, 8.9 Hz, 4H), 3.49 (s, 3H). |
| 3 | Off-White Solid | 150.4-151.4 | | ESIMS m/z 499 ([M + H]$^+$) | $^1$H NMR (400 MHz, Acetone-d$_6$) δ 12.37 (s, 1H), 7.56-7.26 (m, 1H), 6.76 (d, J = 4.1 Hz, 1H), 6.29 (s, 1H), 5.20 (q, J = 8.6 Hz, 4H), 3.60 (s, 3H). |
| 4 | Off-White Solid | 118.1-119.3 | | ESIMS m/z 527 ([M − H]$^+$) | $^1$H NMR (400 MHz, Acetone-d$_6$) δ 11.84 (s, 1H), 7.41-7.28 (m, 1H), 6.66 (d, J = 4.1, 0.9 Hz, 1H), 6.18 (s, 1H), 5.54 (s, 2H), 5.02 (q, J = 8.6 Hz, 4H), 3.27 (s, 3H). |
| 5 | Off-White Solid | 138.7-140.7 | | ESIMS m/z 555 ([M − H]$^+$) | $^1$H NMR (400 MHz, Acetone-d$_6$) δ 12.00 (s, 1H), 7.32-7.24 (m, 1H), 6.69 (d, J = 4.2, 0.9 Hz, 1H), 6.23 (s, 1H), 6.16 (s, 2H), 5.02 (q, J = 8.6 Hz, 4H), 1.89 (s, 3H). |
| 6 | Off-White Solid | 113.1-114.3 | | ESIMS m/z 513 ([M + H]$^+$) | $^1$H NMR (400 MHz, Acetone-d$_6$) δ 7.35-7.24 (m, 1H), 6.73 (d, J = 4.2 Hz, 1H), 5.88 (s, 1H), 4.76 (q, J = 8.7 Hz, 4H), 3.35 (s, 3H), 3.28 (s, 3H). |
| 7 | Off-White Solid | 95.0-96.3 | | ESIMS m/z 512 ([M − CH$_2$O]$^+$) | $^1$H NMR (400 MHz, Acetone-d$_6$) δ 7.35-7.24 (m, 1H), 6.73 (d, J = 4.2 Hz, 1H), 5.88 (s, 1H), 4.76 (q, J = 8.7 Hz, 4H), 3.35 (s, 3H), 3.28 (s, 3H). |
| 8 | Off-White Solid | 176.7-177.9 | | ESIMS m/z 512 ([M − CH$_2$CO$_2$]$^+$) | $^1$H NMR (400 MHz, Acetone-d$_6$) δ 7.32 (s, 1H), 6.76 (s, 1H), 6.00 (s, 1H), 5.83 (s, 2H), 4.76 (d, J = 8.4 Hz, 4H), 3.30 (d, J = 3.1 Hz, 3H), 1.92 (s, 3H). |
| 9 | Off-White Solid | 69.3-70.8 | | ESIMS m/z 512 ([M − PhCHO]+) 496 ([M − PhCH$_2$OCH$_3$]$^+$) | $^1$H NMR (400 MHz, Acetone-d$_6$) δ 7.38-7.01 (m, 6H), 6.75 (d, J = 4.1 Hz, 1H), 5.96 (s, 1H), 5.46 (s, 2H), 4.79-4.57 (m, 6H), 3.34 (s, 3H). |
| 10 | Pale Yellow Gum | | IR (thin film, cm$^{-1}$) 1588, 1302, 1265, | ESIMS m/z 649 ([M + H]$^+$) | $^1$H NMR (400 MHz, Acetone-d$_6$) δ 7.29-7.08 (m, 6H), 6.82 (d, J = 3.9 Hz, 1H), 5.90 (s, 1H), 5.40 (s, |

TABLE 2-continued

| NO. | Appearance | MP (° C.) | IR (cm⁻¹) | MASS | NMR |
|---|---|---|---|---|---|
| | | | 1150, 1066, 996, 958, 697 | | 2H), 5.10 (s, 2H), 4.79 (q, J = 8.7 Hz, 4H), 4.69 (s, 2H), 3.27 (s, 3H). |
| 11 | Pale Yellow Gum | | IR (thin film, cm⁻¹) 1588, 1368, 1263, 1150, 1055, 957, 738, 696 | ESIMS m/z 617 ([M − PhCH₂O]⁺) | ¹H NMR (400 MHz, Acetone-d₆) δ 7.29-7.05 (m, 11H), 6.87 (d, J = 4.0 Hz, 1H), 5.90 (s, 1H), 5.40 (s, 2H), 5.23 (s, 2H), 4.75 (q, J = 8.7 Hz, 4H), 4.69 (s, 2H), 4.52 (s, 2H). |
| 12 | Pale Yellow Solid | 180.9-182.6 | | ESIMS m/z 503 ([M + H]+) 501 ([M − H]+) | ¹H NMR (400 MHz, Acetone-d₆) δ 10.97 (s, 1H), 9.60 (s, 1H), 7.26 (s, 1H), 6.63 (s, 1H), 5.10 (dd, J = 16.9, 8.4 Hz, 4H). |
| 13 | Off White Solid | 78.5-80.3 | | ESIMS m/z 517 ([M + H]⁺) 515 ([M − H]⁺) | ¹H NMR (400 MHz, Acetone-d₆) δ 9.19 (bs, 1H), 17.34-7.20 (m, 1H), 6.66 (d, J = 4.2 Hz, 1H), 4.92 (q, J = 8.6 Hz, 5H), 3.52 (s, 3H). |
| 14 | Off White Solid | 132.8-135.5 | | ESIMS m/z 517 ([M + H]⁺) 515 ([M − H]⁺) | ¹H NMR (400 MHz, Acetone-d₆) δ 11.81 (s, 1H), 7.44-7.39 (m, 1H), 6.78 (dd, J = 4.1, 0.8 Hz, 1H), 5.29 (q, J = 8.5 Hz, 4H), 3.58 (s, 3H). |
| 15 | Off White Solid | 124.6-126.3 | | ESIMS m/z 545 ([M − H]⁺) | ¹H NMR (400 MHz, Acetone-d₆) δ 11.38 (s, 1H), 7.42 (m, 1H), 6.81 (d, J = 4.1 Hz, 1H), 5.62 (s, 2H), 5.25 (q, J = 8.5 Hz, 4H), 3.42 (s, 3H). |
| 16 | Off White Solid | 91.3-92.8 | | ESIMS m/z 620 ([M − H]⁺) | ¹H NMR (400 MHz, Acetone-d₆) δ 11.21 (s, 1H), 7.29-7.23 (m, 1H), 7.21-7.08 (m, 5H), 6.65 (dd, J = 4.1, 0.9 Hz, 1H), 5.64 (s, 2H), 5.04 (q, J = 8.5 Hz, 4H), 4.59 (s, 2H). |
| 17 | Off White Solid | 118.1-119.2 | | ESIMS m/z 531 ([M + H]⁺) | ¹H NMR (400 MHz, Acetone-d₆) δ 7.46 (s, 1H), 6.87 (s, 1H), 4.98 (q, J = 8.4 Hz, 4H), 3.52-3.43 (m, 3H), 3.42-3.35 (m, 3H). |
| 18 | Off White Solid | 139.6-141.0 | | ESIMS m/z 530 ([M − CH₂O]⁺) 514 ([M − CH₃OCH₃]⁺) | ¹H NMR (400 MHz, Acetone-d₆) δ 7.47 (s, 1H), 6.88 (s, 1H), 5.41 (s, 2H), 4.98 (q, J = 8.5 Hz, 4H), 3.49 (m, 6H). |
| 19 | Off White Solid | 114.5-115.5 | | ESIMS m/z 530 ([M − CH₂CO₂]⁺) | ¹H NMR (400 MHz, Acetone-d₆) δ 7.48 (s, 1H), 6.91 (s, 1H), 5.98-5.90 (m, 2H), 5.12-4.85 (m, 4H), 3.57-3.36 (m, 3H), 2.18-1.98 (m, 4H). |
| 20 | Off-White Solid | 237-247 | | ESIMS m/z 477 ([M − H]⁺) (Cl isomer), 523 ([M − H]⁺) (Br isomer) | ¹H NMR (400 MHz, DMSO-d₆) δ 10.92 (s, 1H), 10.49 (s, 1H), 6.55 (s, 0.6H), 6.53 (s, 0.4H), 6.30 (s, 1H), 5.15 (q, J = 8.9 Hz, 6H), 2.67 |

TABLE 2-continued

| NO. | Appearance | MP (° C.) | IR (cm⁻¹) | MASS | NMR |
|---|---|---|---|---|---|
| 21 | Off-White Solid | 81-83 | | ESIMS m/z 493 ([M + H]⁺) | (dd, J = 14.7, 7.3 Hz, 3H), 1.18 (t, J = 7.5 Hz, 4H). $^1$H NMR (300 MHz, DMSO-d$_6$) δ 10.09 (s, 1H), 6.63 (s, 1H), 6.25 (s, 1H) 5.03 (q, J = 9.0 Hz, 4H), 3.39 (s, 3H), 2.69 (q, J = 7.5 Hz, 2H), 1.18 (t, J = 7.6 Hz, 3H). |
| 22 | Off-White Solid | 224-228 | | ESIMS m/z 449 ([M − H]⁺) | $^1$H NMR (400 MHz, DMSO-d$_6$) δ 11.05 (s, 1H), 10.57 (s, 1H), 6.93 (s, 1H), 6.51 (s, 1H), 6.32 (s, 1H), 5.15 (d, J = 8.5 Hz, 4H). |
| 23 | Off-White Solid | 251-254 | | ESIMS m/z 431 ([M + H]⁺) | $^1$H NMR (400 MHz, DMSO-d$_6$) δ 10.91 (s, 1H), 10.39 (s, 1H), 6.59-6.55 (m, 1H), 6.51 (d, J = 1.6 Hz, 1H), 6.30 (s, 1H), 5.14 (q, J = 8.9 Hz, 4H), 2.14 (d, J = 0.8 Hz, 3H). |
| 24 | Off-White Solid | 269-271 | | ESIMS m/z 440 ([M − H]⁺) | $^1$H NMR (300 MHz, DMSO-d$_6$) δ 11.03 (bs, 2H), 7.77 (d, J = 4.2 Hz, 1H), 6.75 (d, J = 4.2 Hz, 1H), 6.34 (s, 1H) 5.15 (q, J = 8.9 Hz, 4H). |
| 25 | Off-White Solid | 221-234 | | ESIMS m/z 481 ([M + H]⁺) | $^1$H NMR (300 MHz, DMSO-d$_6$) δ 11.14 (s, 1H), 10.59 (s, 1H), 7.05 (s, 1H), 6.36 (s, 1H), 5.10 (q, J = 8.9 Hz, 4H), 3.81 (s, 3H). |
| 26 | Off-White Solid | 140-144 | | ESIMS m/z 539 ([M − H]⁺) | $^1$H NMR (300 MHz, DMSO-d$_6$) δ 10.04 (s, 1H), 7.76 (d, J = 8.6 Hz, 2H), 7.54-7.39 (m, 3H), 7.23 (d, J = 1.7 Hz, 1H), 6.25 (s, 1H), 5.03 (q, J = 9.0 Hz, 4H), 3.51 (s, 3H). |
| 27 | Off-White Solid | 264-268 | | ESIMS m/z 440 ([M − H]⁺) | $^1$H NMR (400 MHz, DMSO-d$_6$) δ 11.13 (s, 1H), 10.63 (s, 1H), 8.02 (d, J = 1.6 Hz, 1H), 6.99 (d, J = 1.7 Hz, 1H), 6.34 (s, 1H), 5.16 (q, J = 8.9 Hz, 4H). |
| 28 | Ash Solid | 93-97 | | ESIMS m/z 465 ([M + H]⁺) | $^1$H NMR (400 MHz, DMSO-d$_6$) δ 9.42 (s, 1H), 7.59 (d, J = 5.9 Hz, 1H), 7.05 (d, J = 5.9 Hz, 1H), 6.22 (s, 1H), 5.02 (q, J = 9.0 Hz, 4H), 3.24 (s, 3H). |
| 29 | Off-White Solid | 115-118 | | ESIMS m/z 465 ([M + H]⁺) (Cl isomer), 510 ([M + H]⁺) (Br isomer) | $^1$H NMR (400 MHz, DMSO-d$_6$) δ 10.16 (s, 1H), 7.16 (d, J = 1.7 Hz, 0.2H), 7.05 (d, J = 1.7 Hz, 0.8H), 6.76 (d, J = 1.7 Hz, 0.2 H), 6.74 (d, J = 1.7 Hz, 0.8H), 6.27 (s, 1H), 5.03 (q, J = 9.0 Hz, 5H), 3.43 (s, 3H). |

TABLE 2-continued

| NO. | Appearance | MP (° C.) | IR (cm⁻¹) | MASS | NMR |
|---|---|---|---|---|---|
| 30 | Ash Solid | 220 (dec) | | ESIMS m/z 575 ([M + H]⁺) | ¹H NMR (400 MHz, DMSO-d₆) δ 11.42 (s, 1H), 10.79 (s, 1H), 7.21 (s, 1H), 6.40 (s, 1H), 5.10 (q, J = 8.8 Hz, 4H). |
| 31 | Pale-Yellow Sticky Solid | | | ESIMS m/z 445 ([M + H]⁺) | ¹H NMR (400 MHz, cdcl3) δ 7.33-7.12 (m, 2H), 6.91 (d, J = 5.7 Hz, 1H), 5.94 (s, 1H), 4.73 (q, J = 8.4 Hz, 4H), 3.30 (s, 3H), 2.17 (s, 3H). |
| 32 | Ash Solid | 240 (dec) | | ESIMS m/z 451 ([M + H]⁺) | ¹H NMR (400 MHz, DMSO-d₆) δ 11.16 (s, 1H), 10.69 (s, 1H), 7.18 (d, J = 5.8 Hz, 1H), 6.95 (d, J = 5.8 Hz, 1H), 6.38 (s, 1H), 5.12 (q, J = 8.9 Hz, 4H). |
| 33 | Light-Green Solid | 253-257 | | ESIMS m/z 447 ([M + H]⁺) | ¹H NMR (400 MHz, DMSO-d₆) δ 10.81 (s, 1H), 10.54 (s, 1H), 7.15-6.77 (m, 2H), 6.31 (s, 1H), 5.12 (q, J = 8.9 Hz, 4H), 3.82 (s, 3H). |
| 34 | Off-White Solid | 136-139 | | ESIMS m/z 445 ([M + H]⁺) | ¹H NMR (300 MHz, DMSO-d₆) δ 9.79 (s, 1H), 6.70 (s, 1H), 6.63 (d, J = 1.5 Hz, 1H), 6.22 (s, 1H), 5.02 (q, J = 9.0 Hz, 4H), 3.38 (s, 3H), 2.17 (s, 3H). |
| 35 | Light-Yellow Solid | 107-110 | | ESIMS m/z 495 ([M + H]⁺) | ¹H NMR (300 MHz, DMSO-d₆) δ 9.53 (s, 1H), 7.49 (s, 1H), 6.23 (s, 1H), 5.03 (q, J = 9.0 Hz, 4H), 3.87 (d, J = 2.7 Hz, 3H), 3.24 (s, 3H). |
| 36 | Brown Solid | 107-111 | | ESIMS m/z 461 ([M + H]⁺) | ¹H NMR (300 MHz, DMSO-d₆) δ 8.78 (s, 1H), 7.40 (d, J = 6.1 Hz, 1H), 7.02 (d, J = 6.1 Hz, 1H), 6.19 (s, 1H), 5.01 (q, J = 9.0 Hz, 4H), 3.83 (s, 3H), 3.15 (s, 3H). |
| 37 | Off-White Solid | 249-253 | | ESIMS m/z 431 ([M + H]⁺) | ¹H NMR (300 MHz, DMSO-d₆) δ 10.68 (s, 1H), 10.36 (s, 1H), 6.97 (d, J = 5.5 Hz, 1H), 6.76 (d, J = 5.5 Hz, 1H), 6.34 (s, 1H), 5.10 (q, J = 8.9 Hz, 4H), 2.17 (s, 3H). |
| 38 | Light-Green Solid | 132-136 | | ESIMS m/z 454 ([M − H]⁺) | ¹H NMR (400 MHz, DMSO-d₆) δ 10.26 (s, 1H), 8.02 (d, J = 1.4 Hz, 1H), 7.08 (s, 1H), 6.25 (s, 1H), 5.03 (q, J = 9.0 Hz, 4H), (3.46 (s, 3H). |
| 39 | Light Brown Solid | 112-116 | | ESIMS m/z 445 ([M + H]⁺) | ¹H NMR (400 MHz, DMSO-d₆) δ 9.62 (s, 1H), 6.61 (s, 2H), 6.21 (s, 1H), 5.01 (q, J = 9.0 Hz, 4H), 3.34 (s, 3H), 2.36 (s, 3H). |
| 40 | Off-White Solid | 269-272 | | ESIMS m/z 527 ([M + H]⁺) | ¹H NMR (400 MHz, DMSO-d₆) δ 11.13 (s, 1H), 10.52 (s, 1H), 7.64 (d, J = 8.5 Hz, 2H), 7.48 (d, J = 8.5 Hz, 2H), 7.39 (d, J = 1.5 Hz, 1H), |

TABLE 2-continued

| NO. | Appearance | MP (° C.) | IR (cm$^{-1}$) | MASS | NMR |
|---|---|---|---|---|---|
| 41 | Off-White Solid | 247-250 | | ESIMS m/z 431 ([M + H]$^+$) | 7.07 (d, J = 1.5 Hz, 1H), 6.33 (s, 1H), 5.19 (q, J = 8.9 Hz, 4H). $^1$H NMR (400 MHz, DMSO-d$_6$) δ 10.84 (s, 1H), 10.37 (s, 1H), 6.55 (dd, J = 3.5, 1.0 Hz, 1H), 6.46 (d, J = 3.6 Hz, 1H), 6.29 (s, 1H), 5.14 (q, J = 8.9 Hz, 4H), 2.35 (s, 3H). |
| 42 | Off-White Solid | 237-240 | | ESIMS m/z 465 ([M + H]$^+$) | $^1$H NMR (300 MHz, DMSO-d$_6$) δ 10.85 (s, 1H), 10.42 (s, 1H), 7.08 (s, 1H), 6.36 (s, 1H), 5.10 (q, J = 8.9 Hz, 4H), 2.13 (s, 3H). |
| 43 | Off-White Solid | 217-220 | | ESIMS m/z 449 ([M − H]$^+$) (Cl isomer), 495 ([M − H]$^+$) ( Br isomer) | $^1$H NMR (400 MHz, DMSO-d$_6$) δ 7.10 (d, J = 1.7 Hz, 0.2H), 6.99 (d, J = 1.8 Hz, 0.8H), 6.67-6.64 (m, 1H), 6.31 (s, 1H), 5.15 (q, J = 8.9 Hz, 4H). |
| 44 | Off-White Solid | 210 (dec) | | ESIMS m/z 520 ([M + H]$^+$) | $^1$H NMR (400 MHz, DMSO-d$_6$) δ 11.46 (s, 1H), 10.86 (s, 1H), 6.41 (s, 1H), 5.12 (q, J = 8.8 Hz, 4H). |
| 45 | Off-White Solid | 231-235 | | ESIMS m/z 495 ([M + H]$^+$) | $^1$H NMR (400 MHz, DMSO-d$_6$) δ 11.28 (s, 1H), 10.68 (s, 1H), 7.19 (d, J = 5.8 Hz, 1H), 6.98 (d, J = 5.8 Hz, 1H), 6.39 (s, 1H), 5.11 (q, J = 8.8 Hz, 4H). |

Example 9

Insecticidal Testing

Compounds 1-19 identified in Table 1 were tested against corn earworm (*Helicoverpa zea*) and beet armyworm (*Spodoptera exigua*), and Compounds 20-45 were tested against beet armyworm (*Spodoptera exigua*) and cabbage looper (*Trichoplusia ni* (Huebner)). Beet armyworm has few effective parasites, diseases, or predators to lower its population. Beet armyworm infests many weeds, trees, grasses, legumes, and field crops. In various places, it is of economic concern upon asparagus, cotton, corn, soybeans, tobacco, alfalfa, sugar beets, peppers, tomatoes, potatoes, onions, peas, sunflowers, and citrus, among other plants. Corn earworm is known to attack corn and tomatoes, but it also attacks artichoke, asparagus, cabbage, cantaloupe, collards, cowpeas, cucumbers, eggplant, lettuce, lima beans, melon, okra, peas, peppers, potatoes, pumpkin, snap beans, spinach, squash, sweet potatoes, and watermelon, among other plants. Corn earworm is also known to be resistant to certain insecticides. The cabbage looper is found throughout Canada, Mexico, and the United States wherever crucifers are cultivated. Cabbage loopers are leaf feeders, and in the first three instars they confine their feeding to the lower leaf surface. The cabbage looper feeds on a wide variety of cultivated plants and weeds. As the common name implies, it feeds readily on crucifers, and has been reported damaging broccoli, cabbage, cauliflower, Chinese cabbage, collards, kale, mustard, radish, rutabaga, turnip, and watercress. Other vegetable crops injured include beet, cantaloupe, celery, cucumber, lima bean, lettuce, parsnip, pea, pepper, potato, snap bean, spinach, squash, sweet potato, tomato, and watermelon. It is somewhat erratic in occurrence, typically very abundant one year, and then scarce for two to three years. This is likely due to a nuclear polyhedrosis virus. The cabbage looper is highly dispersive, and adults have sometimes found at high altitudes and far from shore. Flight ranges of approximately 200 km have been estimated. Consequently, because of the above factors control of these pests is important. Furthermore, compounds that control these pests are useful in controlling other pests.

The testing of Compounds 1-19 against corn earworm and beet armyworm was conducted as follows. Bioassays were conducted using a 128 well diet tray assay. To prepare test solutions, the test compound was formulated at 2000 ppm solution as 4 mg/2 mL of 9 acetone:1 tap water. 50 μL of the 2000 ppm (equivalent to 50 μg/cm$^2$ dose on diet surface area) test solution was pipetted upon the surface of 1 mL of lepidopteran diet (Southland Multi-Species Lepidopteran Diet) contained in each of eight wells per insect species (one well=1 replication). A second-instar corn earworm and beet armyworm were placed upon the treated diet in each well once the solvent had air-dried. Trays containing the treated diet and larvae were covered and then held in a growth chamber at 25° C., 50-55% RH, and 16 hr light:8 hr dark for 5 days. Observations were conducted 5 days after treatment and infestation. The number of dead insects of 8 per species per treatment was then determined using a dosing equivalent to 50 μg/cm$^2$ dose on diet surface area.

The testing of Compounds 20-45 against corn earworm and cabbage looper was conducted as follows. Bioassays were conducted using a 128 well diet tray assay. Test compounds were formulated at 2000 ppm solution as 4 mg of compound dissolved in 2 mL of 9 part acetone to 1 part tap water. 50 μl of the 2000 ppm (equivalent to 50 μg/cm² dose on diet surface area) test solution was dispensed upon the surface of 1 mL of lepidopteran diet (Southland Multi-Species Lepidopteran Diet) contained in each of eight wells per insect species (8 wells=1 replication). Acetone was allowed to dry for 10-20 minutes in fume hood. A second-instar beat armyworm and cabbage looper were placed upon the treated diet in each well once the solvent had dried. Trays containing the treated diet and larvae were covered and then held in a growth chamber at 25° C., 50-55% RH, and 16 hour light:8 hour dark for 5 days. Observations were conducted 5 days after treatment and infestation. The number of dead insects of 8 per species per treatment was then determined.

For corn earworm, Compounds 1-2, 4-5, 7-10, 12-13 and 19 showed a percent control or mortality rate of between 80-100%. No activity against corn earworm was noticed in Compounds 3, 6, 11 and 14-18 in the present test. For beet armyworm, Compounds 2, 4-5, 7-10, 12-13, 15, 19, 25-26, 32, 37, and 44 showed a percent control or mortality rate of between 80-100%. Compounds 1, 28, and 45 showed some activity but it was below the 80% threshold of the study. No activity was noticed against beet armyworm in Compounds 3, 6, 11, 14-16-18, 20-24, 27, 29-31, 33-36, and 38-43 in the present test. For cabbage looper, Compounds 25-26, 34, 38-39, and 44 showed a percent control or mortality rate of between 80-100%. Compounds 31 and 35-37 showed some activity but it was below the 80% threshold of the study. No activity was noticed in Compounds 20-24, 27-30, 32-33, 40-43, and 45 in the present test.

The foregoing is illustrative of the present invention, and is not to be construed as limiting thereof. The invention is defined by the following claims, with equivalents of the claims to be included therein.

What is claimed is:

1. A compound of formula (I):

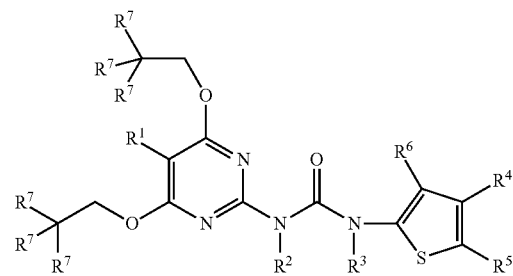

wherein:
$R^1$ represents H or halogen;
$R^2$ represents H or a substituted or unsubstituted $C_1$-$C_6$ alkoxy;
$R^3$ represents H, a substituted or unsubstituted $C_1$-$C_6$ alkyl, or a substituted or unsubstituted $C_1$-$C_6$ alkoxy;
$R^4$ represents H;
$R^5$ represents a substituted or unsubstituted $C_1$-$C_6$ haloalkyl;
$R^6$ represents H; and
$R^7$ represents halogen.

2. A compound according to claim 1, wherein $R^7$ represents F.

3. A compound according to claim 2, wherein $R^5$ represents $CF_3$.

4. A compound according to claim 3, wherein $R^2$ represents H, $CH_2OCH_3$, $CH_2C(=O)CH_3$ or $CH_2OCH_2R^8$, wherein $R^8$ represents

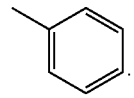

5. A compound according to claim 4, wherein $R^3$ represents H, methyl, $CH_2OCH_3$, or $CH_2OCH_2R^8$, wherein $R^8$ represents

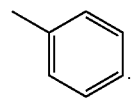

6. A compound according to claim 1, wherein $R^5$ represents $CF_3$.

7. A compound according to claim 6, wherein each of $R^1$, $R^4$, and $R^6$ represents H and $R^7$ represents F.

8. A compound according to claim 7, wherein $R^3$ represents H or methyl.

9. A compound according to claim 1, having the following structure:

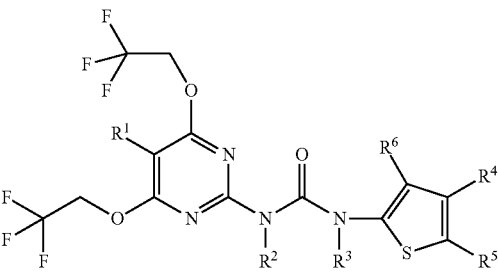

wherein:
$R^1$ represents H or F;
$R^2$ represents H, $CH_2OCH_3$, $CH_2C(=O)CH_3$ or $CH_2OCH_2R^9$, wherein $R^9$ represents

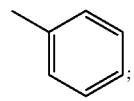

$R^3$ represents H, methyl or $CH_2OCH_3$;
$R^4$ represents H;
$R^5$ represents $CF_3$; and
$R^6$ represents H.

10. A composition for controlling insects which comprises a compound according to claim 1 in combination with a phytologically-acceptable carrier.

11. A method of controlling insects which comprises applying to a locus where control is desired an insect-inactivating amount of a compound according to claim 1.

12. A composition which comprises a compound according to claim 1 and at least one compound selected from the group consisting of fungicides, insecticides, nematocides, miticides, arthropodicides, and bactericides.

13. A composition which comprises a compound according to claim 1 and one or more compounds selected from: (3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butomethyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 21P, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluoron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cyclopro-thrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfuram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdepallethrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butomethyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, fluorochloridone, fluoroxypyr, fluoroxypyr-butomethyl, fluoroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminum, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexylure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluoron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluoron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfuram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluoron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluoron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid.

\* \* \* \* \*